US007585943B2

(12) United States Patent
Kim et al.

(10) Patent No.: US 7,585,943 B2
(45) Date of Patent: Sep. 8, 2009

(54) COMPOSITIONS AND METHODS FOR FUSION PROTEIN SEPARATION

(75) Inventors: Sujeong Kim, Seoul (KR); Jong-Mook Kim, Seoul (KR); Song Shan Xu, Beijing (CN)

(73) Assignee: ViroMed Co., Ltd., Seoul (KR)

( * ) Notice: Subject to any disclaimer, the term of this patent is extended or adjusted under 35 U.S.C. 154(b) by 0 days.

(21) Appl. No.: 11/407,336

(22) Filed: Apr. 20, 2006

(65) Prior Publication Data

US 2006/0276625 A1 Dec. 7, 2006
US 2008/0171852 A9 Jul. 17, 2008

Related U.S. Application Data

(60) Provisional application No. 60/672,879, filed on Apr. 20, 2005.

(51) Int. Cl.
 C07K 5/00 (2006.01)
 C07K 14/00 (2006.01)
 C12N 9/00 (2006.01)
 C07K 14/52 (2006.01)
 C07K 16/00 (2006.01)
 C07K 2/00 (2006.01)
 C07K 4/00 (2006.01)
 C07K 14/54 (2006.01)
 C07K 14/555 (2006.01)
 C07K 14/575 (2006.01)
 C07K 14/705 (2006.01)

(52) U.S. Cl. ............... 530/350; 530/300; 530/351; 530/387.3; 530/395; 530/397; 530/398; 530/399; 530/402; 435/183

(58) Field of Classification Search .............. None
See application file for complete search history.

(56) References Cited

U.S. PATENT DOCUMENTS

| 6,551,795 B1 * | 4/2003 | Rubenfield et al. .......... 435/69.1 |
| 2003/0109021 A1 | 6/2003 | Wu et al. |
| 2004/0210036 A1 | 10/2004 | Dwyer et al. |

FOREIGN PATENT DOCUMENTS

| JP | 2005-49164 | 2/2005 |
| WO | WO 93/00365 A2 | 1/1993 |
| WO | WO 95/23814 A1 | 9/1995 |
| WO | WO 02/083919 A2 | 10/2002 |
| WO | WO 02/083921 A2 | 10/2002 |
| WO | WO 2004/011650 A2 | 2/2004 |
| WO | WO 2005/007090 A2 | 1/2005 |
| WO | WO 2005/035003 A2 | 4/2005 |
| WO | WO 2006/015385 A2 | 2/2006 |
| WO | WO 2006/038208 A2 | 4/2006 |

OTHER PUBLICATIONS

Paul et al., Molecular cloning of a cDNA encoding interleukin 11, a stromal cell-derived lymphopoietic and hematopoietic cytokine, Proc Natl Acad Sci. 1990, 87(19): 7512-7516.*

Ngo et al., in The Protein Folding Problem and Tertiary Structure Prediction, 1994, Merz et al. (ed.), Birkhauser, Boston, MA, pp. 433 and 492-495.*
Schneider et al. (J. Biol. Chem., 277(12): pp. 9944-9951, 2002).*
"Thrombin factor IIa"—Sigma-Aldrich catalog, Retrieved from the Internet: <http://www.sigmaaldrich.com/life-science/metabolomics/enzyme-explorer/analytical-enzymes/thrombins.html>.*
Kahn, M.L., et al., "A dual thrombin receptor system for platelet activation," *Nature* 394:690-694, Macmillan Publishers Ltd. (1998).
Takagi, T., and Doolittle, R.F., "Amino Acid Sequence Studies on Factor XIII and the Peptide Released During Its Activation by Thrombin," *Biochemistry* 13:750-756, American Chemical Society (1974).
Binnie, C.G., and Lord, S.T., "The Fibrinogen Sequences That Interact With Thrombin," *Blood* 81:3186-3192, The American Society of Hematology (1993).
Chang, J.-Y., "Thrombin specificity. Requirement for apolar amino acids adjacent to the thrombin cleavage site of polypeptide substrate," *Eur. J. Biochem.* 151:217-224, Blackwell Science Inc. (1985).
GST gene fusion system handbook, Amersham Biosciences, Edition AA, p. 88-89 (2002).
Guan, K.L., and Dixon, J.E., "Eukaryotic Proteins Expressed in *Eschericha coli*: An Improved Thrombin Cleavage and Purification Procedure of Fusion Proteins with Glutathione S-Transferase," *Anal. Biochem.* 192:262-267, Academic Press, Inc. (1991).
Hakes, D.J., and Dixon, J.E., "New Vectors for High Level Expression of Recombinant Proteins in Bacteria," *Anal. Biochem.* 202:293-298, Academic Press, Inc. (1992).
Jenny, R.J., et al., "A critical review of the methods for cleavage of fusion proteins with thrombin and factor Xa," *Protein Expr. Purif.* 31:1-11, Academic Press (2003).
Porse, B.T., et al., "The Antibiotic Thiostrepton Inhibits a Functional Transition Within Protein L11 at the Ribosomal GTPase Centre," *J. Mol. Biol.* 276:391-404, Academic Press Limited (1998).
Raftery, M.J., et al., "Overexpression, Oxidative Refolding, and Zinc Binding of Recombinant Forms of the Murine S100 Protein MRP14 (S100A9)," *Protein Expr. Purif.* 15:228-235, Academic Press (1999).
Schlumpberger, M., et al., "The prion domain of yeast Ure2p induces autocatalytic formation of amyloid fibers by a recombinant fusion protein," *Protein Sci.* 9:440-451, Cold Spring Harbor Laboratory Press (2000).
Taylor, G.S., et al., "The Activity of Cdc14p, an Oligomeric Dual Specificity Protein Phosphatase from *Saccharomyces cerevisiae*, Is Required for Cell Cycle Progression," *J. Biol. Chem.* 272:24054-24063, The American Society for Biochemistry and Molecular Biology, Inc. (1997).
Wassenberg, D., et al., "Xylanase XynA from the hyperthermophilic bacterium *Thermotoga maritima*: Structure and stability of the recombinant enzyme and its isolated cellulose-binding domain," *Protein Sci.* 6:1718-1726, Cold Spring Harbor Laboratory Press (1997).

(Continued)

*Primary Examiner*—Rebecca E Prouty
*Assistant Examiner*—Jae W Lee
(74) *Attorney, Agent, or Firm*—Sterne, Kessler, Goldstein & Fox P.L.L.C.

(57) ABSTRACT

The present invention relates to compositions and methods for fusion protein separation utilizing a peptide linker comprising a novel thrombin cleavage site.

31 Claims, 10 Drawing Sheets

OTHER PUBLICATIONS

Zaitseva, J., et al., "The proteins encoded by the *rbs* operon of *Escherichia coli*: II. Use of chimeric protein constructs to isolate and characterize RbsC," *Protein Sci.* 5:1100-1107, Cold Spring Harbor Laboratory Press (1996).

Scheerlinck, J.-P. Y., et al., "Redistribution of a Murine Humoral Immune Response Following Removal of an Immunodominant B Cell Epitope From a Recombinant Fusion Protein," *Molec. Immunol.* 30:733-739, Pergamon Press Ltd. (1993).

European extended Search Report for European Application No. 06779979.1, mailed Feb. 18, 2009, European Patent Office, The Netherlands.

* cited by examiner

Fig. 2A

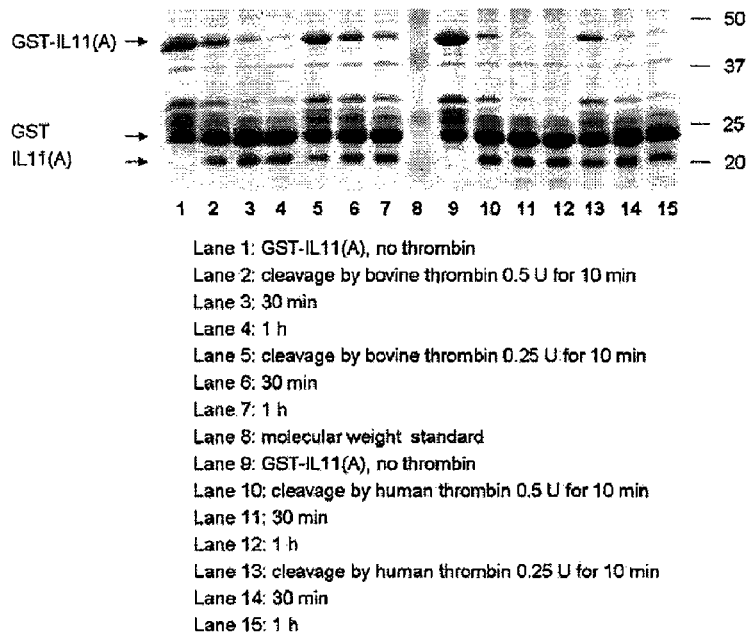

Lane 1: GST-IL11(A), no thrombin
Lane 2: cleavage by bovine thrombin 0.5 U for 10 min
Lane 3: 30 min
Lane 4: 1 h
Lane 5: cleavage by bovine thrombin 0.25 U for 10 min
Lane 6: 30 min
Lane 7: 1 h
Lane 8: molecular weight standard
Lane 9: GST-IL11(A), no thrombin
Lane 10: cleavage by human thrombin 0.5 U for 10 min
Lane 11: 30 min
Lane 12: 1 h
Lane 13: cleavage by human thrombin 0.25 U for 10 min
Lane 14: 30 min
Lane 15: 1 h

Fig. 2B

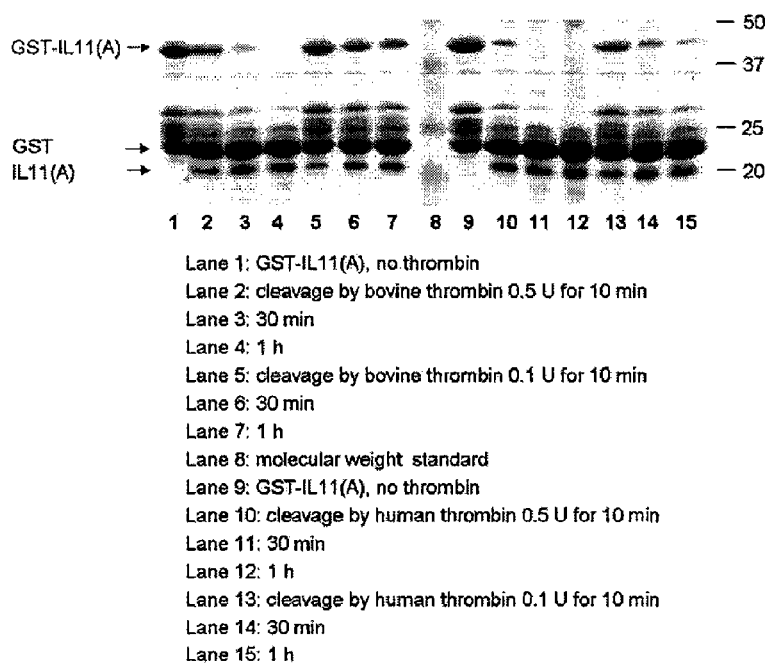

Lane 1: GST-IL11(A), no thrombin
Lane 2: cleavage by bovine thrombin 0.5 U for 10 min
Lane 3: 30 min
Lane 4: 1 h
Lane 5: cleavage by bovine thrombin 0.1 U for 10 min
Lane 6: 30 min
Lane 7: 1 h
Lane 8: molecular weight standard
Lane 9: GST-IL11(A), no thrombin
Lane 10: cleavage by human thrombin 0.5 U for 10 min
Lane 11: 30 min
Lane 12: 1 h
Lane 13: cleavage by human thrombin 0.1 U for 10 min
Lane 14: 30 min
Lane 15: 1 h Lane1 : molecular weight standard
Lane2 : GST-Thymosinß4, no thrombin
Lane3 : cleavage by thrombin for 10 min
Lane4 : 30 min
Lane5 : 1 h
Lane6 : 3 h Lane1 : molecular weight standard
Lane2 : GST-IL6, no thrombin
Lane3 : cleavage by thrombin for 10 min
Lane4 : 30 min
Lane5 : 1 h
Lane6 : 2 h
Lane7 : 3 h Lane1 : molecular weight standard
Lane2 : GST-IL11(LV-), no thrombin
Lane3 : cleavage by thrombin for 10 min
Lane4 : 30 min
Lane5 : 1 h
Lane6 : 2 h
Lane7 : 3 h Lane 1: molecular weight standard
Lane 2: MBP-IL11, no thrombin
Lane 3: cleavage by thrombin for 10min
Lane 4: 30min
Lane 5: 1h
Lane 6: 2h
Lane 7: 3h Lane 1: molecular weight standard
Lane 2: His-IL11, no thrombin
Lane 3: cleavage by thrombin for 10 min
Lane 4: 30 min
Lane 5: 1 h
Lane 6: 2 h
Lane 7: 3 h

SEQUENCE LISTING

<160> NUMBER OF SEQ ID NOS: 42

<210> SEQ ID NO 1
<211> LENGTH: 6
<212> TYPE: PRT
<213> ORGANISM: Artificial sequence
<220> FEATURE:
<223> OTHER INFORMATION: Thrombin cleavage site

<400> SEQUENCE: 1

Leu Val Pro Arg Gly Ser
1               5

<210> SEQ ID NO 2
<211> LENGTH: 6
<212> TYPE: PRT
<213> ORGANISM: Artificial sequence
<220> FEATURE:
<223> OTHER INFORMATION: Thrombin cleavage site

<400> SEQUENCE: 2

Met Tyr Pro Arg Gly Asn
1               5

<210> SEQ ID NO 3
<211> LENGTH: 6
<212> TYPE: PRT
<213> ORGANISM: Artificial sequence

```
<220> FEATURE:
<223> OTHER INFORMATION: Thrombin cleavage site

<400> SEQUENCE: 3

Ile Arg Pro Lys Leu Lys
1               5

<210> SEQ ID NO 4
<211> LENGTH: 5
<212> TYPE: PRT
<213> ORGANISM: Artificial sequence
<220> FEATURE:
<223> OTHER INFORMATION: Thrombin cleavage site

<400> SEQUENCE: 4

Leu Val Pro Arg Gly
1               5

<210> SEQ ID NO 5
<211> LENGTH: 6
<212> TYPE: PRT
<213> ORGANISM: Artificial sequence
<220> FEATURE:
<223> OTHER INFORMATION: Peptide linker

<400> SEQUENCE: 5

Ser Gly Gly Gly Gly Gly
1               5

<210> SEQ ID NO 6
<211> LENGTH: 12
<212> TYPE: PRT
<213> ORGANISM: Artificial sequence
<220> FEATURE:
<223> OTHER INFORMATION: Cdc14p thrombin cleavage site

<400> SEQUENCE: 6

Ser Gly Gly Gly Gly Gly Leu Val Pro Arg Gly Ser
1               5                   10

<210> SEQ ID NO 7
<211> LENGTH: 8
<212> TYPE: PRT
<213> ORGANISM: Artificial sequence
<220> FEATURE:
<223> OTHER INFORMATION: Peptide linker

<400> SEQUENCE: 7

Pro Arg Gly Ser Pro Arg Ala Ser
1               5

<210> SEQ ID NO 8
<211> LENGTH: 10
<212> TYPE: PRT
<213> ORGANISM: Artificial sequence
<220> FEATURE:
<223> OTHER INFORMATION: Peptide linker

<400> SEQUENCE: 8

Leu Val Pro Arg Gly Ser Pro Arg Ala Ser
1               5                   10

<210> SEQ ID NO 9
<211> LENGTH: 6
<212> TYPE: PRT
<213> ORGANISM: Artificial sequence
<220> FEATURE:
```

<223> OTHER INFORMATION: MRP14 thrombin cleavage site

<400> SEQUENCE: 9

Asn Asn Pro Arg Gly His
1               5

<210> SEQ ID NO 10
<211> LENGTH: 6
<212> TYPE: PRT
<213> ORGANISM: Artificial sequence
<220> FEATURE:
<223> OTHER INFORMATION: Fibrinopeptide A thrombin cleavage site

<400> SEQUENCE: 10

Gly Gly Val Arg Gly Pro
1               5

<210> SEQ ID NO 11
<211> LENGTH: 6
<212> TYPE: PRT
<213> ORGANISM: Artificial sequence
<220> FEATURE:
<223> OTHER INFORMATION: Fibrinopeptide B thrombin cleavage site

<400> SEQUENCE: 11

Phe Ser Ala Arg Gly His
1               5

<210> SEQ ID NO 12
<211> LENGTH: 27
<212> TYPE: DNA
<213> ORGANISM: Artificial sequence
<220> FEATURE:
<223> OTHER INFORMATION: IL-11 PCR primer

<400> SEQUENCE: 12
ggatccccgc gagcttcccc agaccct                                           27

<210> SEQ ID NO 13
<211> LENGTH: 30
<212> TYPE: DNA
<213> ORGANISM: Artificial sequence
<220> FEATURE:
<223> OTHER INFORMATION: IL-11 PCR primer

<400> SEQUENCE: 13
gtcgacccct tatcacagcc gagtcttcag                                        30

<210> SEQ ID NO 14
<211> LENGTH: 27
<212> TYPE: DNA
<213> ORGANISM: Artificial sequence
<220> FEATURE:
<223> OTHER INFORMATION: IL-11 mutagenesis primer

<400> SEQUENCE: 14
ccagccaccc ccgaacccgc cggcgcc                                           27

<210> SEQ ID NO 15
<211> LENGTH: 27
<212> TYPE: DNA
<213> ORGANISM: Artificial sequence
<220> FEATURE:
<223> OTHER INFORMATION: IL-11 mutagenesis primer

<400> SEQUENCE: 15
ggcgccggcg ggttcggggg tggctgg                                          27

<210> SEQ ID NO 16
<211> LENGTH: 4
<212> TYPE: PRT
<213> ORGANISM: Artificial sequence
<220> FEATURE:
<223> OTHER INFORMATION: Partial thrombin cleavage site

<400> SEQUENCE: 16

Pro Arg Ala Ser
1

<210> SEQ ID NO 17
<211> LENGTH: 177
<212> TYPE: PRT
<213> ORGANISM: Artificial sequence
<220> FEATURE:
<223> OTHER INFORMATION: hIL11(A)

<400> SEQUENCE: 17

Leu Val Pro Arg Gly Ser Pro Arg Ala Ser Pro Asp Pro Arg Ala Glu
1               5                   10                  15

Leu Asp Ser Thr Val Leu Leu Thr Arg Ser Leu Leu Ala Asp Thr Arg
            20                  25                  30

Gln Leu Ala Ala Gln Leu Arg Asp Lys Phe Pro Ala Asp Gly Asp His
        35                  40                  45

Asn Leu Asp Ser Leu Pro Thr Leu Ala Met Ser Ala Gly Ala Leu Gly
    50                  55                  60

Ala Leu Gln Leu Pro Gly Val Leu Thr Arg Leu Arg Ala Asp Leu Leu
65                  70                  75                  80

Ser Tyr Leu Arg His Val Gln Trp Leu Arg Arg Ala Gly Gly Ser Ser
                85                  90                  95

Leu Lys Thr Leu Glu Pro Glu Leu Gly Thr Leu Gln Ala Arg Leu Asp
            100                 105                 110

Arg Leu Leu Arg Arg Leu Gln Leu Leu Met Ser Arg Leu Ala Leu Pro
        115                 120                 125

Gln Pro Pro Asn Pro Pro Ala Pro Pro Leu Ala Pro Pro Ser Ser
    130                 135                 140

Ala Tyr Gly Gly Ile Arg Ala Ala His Ala Ile Leu Gly Gly Leu His
145                 150                 155                 160

Leu Thr Leu Asp Trp Ala Val Arg Gly Leu Leu Leu Leu Lys Thr Arg
                165                 170                 175

Leu

<210> SEQ ID NO 18
<211> LENGTH: 33
<212> TYPE: DNA
<213> ORGANISM: Artificial sequence
<220> FEATURE:
<223> OTHER INFORMATION: GST-Thymosin Beta 4 PCR primer

<400> SEQUENCE: 18
ggatcccctc gagcttctga caaacccgat atg                                   33

<210> SEQ ID NO 19
<211> LENGTH: 30
<212> TYPE: DNA
<213> ORGANISM: Artificial sequence
<220> FEATURE:
<223> OTHER INFORMATION: GST-Thymosin Beta 4 PCR primer

```
<400> SEQUENCE: 19
gtcgacttac gattcgcctg cttgcttctc                                    30

<210> SEQ ID NO 20
<211> LENGTH: 6
<212> TYPE: PRT
<213> ORGANISM: Artificial sequence
<220> FEATURE:
<223> OTHER INFORMATION: Partial thrombin cleavage site

<400> SEQUENCE: 20

Gly Ser Pro Arg Ala Ser
1               5

<210> SEQ ID NO 21
<211> LENGTH: 52
<212> TYPE: PRT
<213> ORGANISM: Artificial sequence
<220> FEATURE:
<223> OTHER INFORMATION: Thymosin Beta 4

<400> SEQUENCE: 21

Leu Val Pro Arg Gly Ser Pro Arg Ala Ser Asp Lys Pro Asp Met Ala
1               5                   10                  15

Glu Ile Glu Lys Phe Asp Lys Ser Lys Leu Lys Lys Thr Glu Thr Gln
            20                  25                  30

Glu Lys Asn Pro Leu Pro Ser Lys Glu Thr Ile Glu Gln Glu Lys Gln
        35                  40                  45

Ala Gly Glu Ser
    50

<210> SEQ ID NO 22
<211> LENGTH: 10
<212> TYPE: PRT
<213> ORGANISM: Artificial sequence
<220> FEATURE:
<223> OTHER INFORMATION: Thymosin Beta 4 N-terminal sequence

<400> SEQUENCE: 22

Ala Ser Asp Lys Pro Asp Met Ala Glu Ile
1               5                   10

<210> SEQ ID NO 23
<211> LENGTH: 30
<212> TYPE: DNA
<213> ORGANISM: Artificial sequence
<220> FEATURE:
<223> OTHER INFORMATION: GST-IL6 PCR primer

<400> SEQUENCE: 23
ggatcccctc gagcttcttt ccctacttca                                    30

<210> SEQ ID NO 24
<211> LENGTH: 27
<212> TYPE: DNA
<213> ORGANISM: Artificial sequence
<220> FEATURE:
<223> OTHER INFORMATION: GST-IL6 PCR primer

<400> SEQUENCE: 24
gtcgacctag gtttgccgag tagatct                                       27

<210> SEQ ID NO 25
```

```
<211> LENGTH: 197
<212> TYPE: PRT
<213> ORGANISM: Artificial sequence
<220> FEATURE:
<223> OTHER INFORMATION: IL-6

<400> SEQUENCE: 25

Leu Val Pro Arg Gly Ser Pro Arg Ala Ser Phe Pro Thr Ser Gln Val
1               5                   10                  15

Arg Arg Gly Asp Phe Thr Glu Asp Thr Thr Pro Asn Arg Pro Val Tyr
            20                  25                  30

Thr Thr Ser Gln Val Gly Gly Leu Ile Thr His Val Leu Trp Glu Ile
        35                  40                  45

Val Glu Met Arg Lys Glu Leu Cys Asn Gly Asn Ser Asp Cys Met Asn
    50                  55                  60

Asn Asp Asp Ala Leu Ala Glu Asn Asn Leu Lys Leu Pro Glu Ile Gln
65                  70                  75                  80

Arg Asn Asp Gly Cys Tyr Gln Thr Gly Tyr Asn Gln Glu Ile Cys Leu
                85                  90                  95

Leu Lys Ile Ser Ser Gly Leu Leu Glu Tyr His Ser Tyr Leu Glu Tyr
            100                 105                 110

Met Lys Asn Asn Leu Lys Asp Asn Lys Lys Asp Lys Ala Arg Val Leu
        115                 120                 125

Gln Arg Asp Thr Glu Thr Leu Ile His Ile Phe Asn Gln Glu Val Lys
    130                 135                 140

Asp Leu His Lys Ile Val Leu Pro Thr Pro Ile Ser Asn Ala Leu Leu
145                 150                 155                 160

Thr Asp Lys Leu Glu Ser Gln Lys Glu Trp Leu Arg Thr Lys Thr Ile
                165                 170                 175

Gln Phe Ile Leu Lys Ser Leu Glu Glu Phe Leu Lys Val Thr Leu Arg
            180                 185                 190

Ser Thr Arg Gln Thr
        195

<210> SEQ ID NO 26
<211> LENGTH: 10
<212> TYPE: PRT
<213> ORGANISM: Artificial sequence
<220> FEATURE:
<223> OTHER INFORMATION: IL-6 N-terminal sequence

<400> SEQUENCE: 26

Ala Ser Phe Pro Thr Ser Gln Val Arg Arg
1               5                   10

<210> SEQ ID NO 27
<211> LENGTH: 7
<212> TYPE: PRT
<213> ORGANISM: Artificial sequence
<220> FEATURE:
<223> OTHER INFORMATION: PAR4 thrombin cleavage site

<400> SEQUENCE: 27

Leu Pro Ala Pro Arg Gly Tyr
1               5

<210> SEQ ID NO 28
<211> LENGTH: 30
<212> TYPE: DNA
<213> ORGANISM: Artificial sequence
<220> FEATURE:
```

<223> OTHER INFORMATION: GST-PAR4 PCR primer

<400> SEQUENCE: 28
ggatcccctc gagcttctat gtgggggcga                                    30

<210> SEQ ID NO 29
<211> LENGTH: 27
<212> TYPE: DNA
<213> ORGANISM: Artificial sequence
<220> FEATURE:
<223> OTHER INFORMATION: GST-PAR4 PCR primer

<400> SEQUENCE: 29
gtcgactcag tgcaccaggg ccaggta                                       27

<210> SEQ ID NO 30
<211> LENGTH: 190
<212> TYPE: PRT
<213> ORGANISM: Artificial sequence
<220> FEATURE:
<223> OTHER INFORMATION: PAR4

<400> SEQUENCE: 30

Leu Val Pro Arg Gly Ser Pro Arg Ala Ser Met Trp Gly Arg Leu Leu
1               5                   10                  15

Leu Trp Pro Leu Val Leu Gly Phe Ser Leu Ser Gly Gly Thr Gln Thr
            20                  25                  30

Pro Ser Val Tyr Asp Glu Ser Gly Ser Thr Gly Gly Gly Asp Asp Ser
        35                  40                  45

Thr Pro Ser Ile Leu Pro Ala Pro Arg Gly Tyr Pro Gly Gln Val Cys
    50                  55                  60

Ala Asn Asp Ser Asp Thr Leu Glu Leu Pro Asp Ser Ser Arg Ala Leu
65                  70                  75                  80

Leu Leu Gly Tyr Val Pro Thr Arg Leu Val Pro Ala Leu Tyr Gly Leu
                85                  90                  95

Val Leu Val Val Gly Leu Pro Ala Asn Gly Leu Ala Leu Trp Val Leu
            100                 105                 110

Ala Thr Gln Ala Pro Arg Leu Pro Ser Thr Met Leu Leu Met Asn Leu
        115                 120                 125

Ala Thr Ala Asp Leu Leu Leu Ala Leu Ala Leu Pro Pro Arg Ile Ala
    130                 135                 140

Tyr His Leu Arg Gly Gln Arg Tyr Pro Phe Gly Glu Ala Ala Cys Arg
145                 150                 155                 160

Leu Ala Thr Ala Ala Leu Tyr Gly His Met Tyr Gly Ser Val Leu Leu
                165                 170                 175

Leu Ala Ala Val Ser Leu Asp Arg Tyr Leu Ala Leu Val His
            180                 185                 190

<210> SEQ ID NO 31
<211> LENGTH: 8
<212> TYPE: PRT
<213> ORGANISM: Artificial sequence
<220> FEATURE:
<223> OTHER INFORMATION: IL11 thrombin cleavage site

<400> SEQUENCE: 31

Pro Leu Gly Ser Pro Arg Ala Ser
1               5

<210> SEQ ID NO 32

```
<211> LENGTH: 27
<212> TYPE: DNA
<213> ORGANISM: Artificial sequence
<220> FEATURE:
<223> OTHER INFORMATION: IL11 mutagenesis primer

<400> SEQUENCE: 32 cagggggcccc ggggatcccc tcgagct                                            27

<210> SEQ ID NO 33
<211> LENGTH: 24
<212> TYPE: DNA
<213> ORGANISM: Artificial sequence
<220> FEATURE:
<223> OTHER INFORMATION: IL11 mutagenesis primer

<400> SEQUENCE: 33
agctcgaggg gatccccggg gctg                                                24

<210> SEQ ID NO 34
<211> LENGTH: 175
<212> TYPE: PRT
<213> ORGANISM: Artificial sequence
<220> FEATURE:
<223> OTHER INFORMATION: IL-11(LV)

<400> SEQUENCE: 34
```

Pro Arg Gly Ser Pro Arg Ala Ser Pro Asp Pro Arg Ala Glu Leu Asp
1               5                   10                  15

Ser Thr Val Leu Leu Thr Arg Ser Leu Leu Ala Asp Thr Arg Gln Leu
            20                  25                  30

Ala Ala Gln Leu Arg Asp Lys Phe Pro Ala Asp Gly Asp His Asn Leu
        35                  40                  45

Asp Ser Leu Pro Thr Leu Ala Met Ser Ala Gly Ala Leu Gly Ala Leu
    50                  55                  60

Gln Leu Pro Gly Val Leu Thr Arg Leu Arg Ala Asp Leu Leu Ser Tyr
65                  70                  75                  80

Leu Arg His Val Gln Trp Leu Arg Arg Ala Gly Gly Ser Ser Leu Lys
                85                  90                  95

Thr Leu Glu Pro Glu Leu Gly Thr Leu Gln Ala Arg Leu Asp Arg Leu
            100                 105                 110

Leu Arg Arg Leu Gln Leu Leu Met Ser Arg Leu Ala Leu Pro Gln Pro
        115                 120                 125

Pro Pro Asn Pro Pro Ala Pro Pro Leu Ala Pro Pro Ser Ser Ala Tyr
    130                 135                 140

Gly Gly Ile Arg Ala Ala His Ala Ile Leu Gly Gly Leu His Leu Thr
145                 150                 155                 160

Leu Asp Trp Ala Val Arg Gly Leu Leu Leu Leu Lys Thr Arg Leu
                165                 170                 175

```
<210> SEQ ID NO 35
<211> LENGTH: 10
<212> TYPE: PRT
<213> ORGANISM: Artificial sequence
<220> FEATURE:
<223> OTHER INFORMATION: IL-11(LV) N-terminal sequence

<400> SEQUENCE: 35
```

Ala Ser Pro Asp Pro Arg Ala Glu Leu Asp
1               5                   10

```
<210> SEQ ID NO 36
<211> LENGTH: 30
<212> TYPE: DNA
<213> ORGANISM: Artificial sequence
<220> FEATURE:
<223> OTHER INFORMATION: IL-11(A) PCR primer

<400> SEQUENCE: 36
gaattccctc gaggttcacc tcgagcttcc                                        30

<210> SEQ ID NO 37
<211> LENGTH: 27
<212> TYPE: DNA
<213> ORGANISM: Artificial sequence
<220> FEATURE:
<223> OTHER INFORMATION: IL-11(A) PCR primer

<400> SEQUENCE: 37
gtcgactcac agccgagtct tcagcag                                           27

<210> SEQ ID NO 38
<211> LENGTH: 10
<212> TYPE: PRT
<213> ORGANISM: Artificial sequence
<220> FEATURE:
<223> OTHER INFORMATION: IL-11 N-terminal sequence

<400> SEQUENCE: 38

Ala Ser Pro Asp Pro Arg Ala Glu Leu Asp
1               5                   10

<210> SEQ ID NO 39
<211> LENGTH: 30
<212> TYPE: DNA
<213> ORGANISM: Artificial sequence
<220> FEATURE:
<223> OTHER INFORMATION: His-IL11 PCR primer

<400> SEQUENCE: 39
catatgcctc gaggttcacc tcgagcttcc                                        30

<210> SEQ ID NO 40
<211> LENGTH: 27
<212> TYPE: DNA
<213> ORGANISM: Artificial sequence
<220> FEATURE:
<223> OTHER INFORMATION: His-IL11 PCR primer

<400> SEQUENCE: 40
ggatcctcac agccgagtct tcagcag                                           27

<210> SEQ ID NO 41
<211> LENGTH: 10
<212> TYPE: PRT
<213> ORGANISM: Artificial sequence
<220> FEATURE:
<223> OTHER INFORMATION: IL-11 N-terminal sequence

<400> SEQUENCE: 41

Ala Ser Pro Asp Pro Arg Ala Glu Leu Asp
1               5                   10

<210> SEQ ID NO 42
<211> LENGTH: 15
<212> TYPE: PRT
<213> ORGANISM: Artificial sequence
<220> FEATURE:
```

-continued

```
<223> OTHER INFORMATION: IL11(A)

<400> SEQUENCE: 42

Ala Ser Pro Asp Pro Arg Ala Glu Leu Asp Ser Thr Val Leu Leu
1               5                   10                  15
```

COMPOSITIONS AND METHODS FOR FUSION PROTEIN SEPARATION

BACKGROUND OF THE INVENTION

1. Field of the Invention

The present invention relates to compositions and methods for fusion protein separation.

2. Related Art

Expression systems utilizing fusion proteins are a well-accepted technology for the production of recombinant proteins. In such systems, the fusion partner facilitates the expression and purification of the desired protein. The fusion partner is frequently used to provide a "tag" which can facilitate the subsequent purification of the fusion protein. However, in order to recover the desired protein in its native form or in a pharmaceutically acceptable form, the fusion partner must be removed once the fusion protein is isolated. The most widely used method to remove the fusion partner involves the use of specific cleavage enzymes such as thrombin, factor Xa or enterokinase (Wassenberg et al., *Protein Sci.* 6:1718 (1997); Schlumpberger et al., *Protein Sci.* 9:440 (2000); Zaitseva et al., *Protein Sci.* 5:1100 (1996)). This involves the insertion of a unique amino acid sequence that is specific for cleavage by the cleavage enzyme between the desired protein and the fusion partner. The desired protein can be recovered by the cleavage of the fusion protein with the cleavage enzyme (e.g., thrombin).

Thrombin is a trypsin-like serine protease which will cleave peptide bonds using the serine amino acid. The specificity of thrombin has been studied by a number of investigators. The previously known thrombin cleavage sites are as follows (Chang, *Eur. J. Biochem.* 151:217 (1985); GST gene fusion system handbook, Amersham Biosciences, Edition AA, p. 88-89).

1) P4-P3-Pro-Arg/Lys↓P1'-P2', wherein P3 and P4 are hydrophobic amino acids and P1' and P2' are non-acidic amino acids. The Arg/Lys↓P1' bond is cleaved.

Examples:

|   | P4  | P3  | Pro | Arg/Lys | P1' | P2' |
|---|-----|-----|-----|---------|-----|-----|
| A | Leu | Val | Pro | Arg     | Gly | Ser |
| B | Met | Tyr | Pro | Arg     | Gly | Asn |
| C | Ile | Arg | Pro | Lys     | Leu | Lys |

(SEQ ID NOS:1-3)

2) P2-Arg/Lys↓P1', wherein either P2 or P1' is Gly. The Arg/Lys↓P1' bond is cleaved.

Examples:

|   | P2  | Arg/Lys | P1' |
|---|-----|---------|-----|
| A | Ala | Arg     | Gly |
| B | Gly | Lys     | Ala |

The most frequently used thrombin cleavage sequence is Leu-Val-Pro-Arg-Gly (SEQ ID NO:4) or Leu-Val-Pro-Arg-Gly-Ser (SEQ ID NO:1), which is derived from the sequence in bovine factor XIII (Takagi et al., *Biochemistry* 13:750 (1974)). Cleavage occurs at the arginine residue, resulting in the protein of interest being extended at its amino-terminal end by either a Gly or Gly-Ser. This thrombin cleavage sequence is also adopted in several commercially available expression plasmids, including the pGEX series (Amersham Biosciences) and the pET series (Novagen).

More recently, the Leu-Val-Pro-Arg-Gly-Ser (SEQ ID NO:1) sequence was further modified to include a glycine-rich linker containing the sequence Ser-Gly-Gly-Gly-Gly-Gly (SEQ ID NO:5) located immediately before or after the thrombin cleavage site Leu-Val-Pro-Arg-Gly-Ser (SEQ ID NO:1) (Guan et al., *Anal. Biochem.* 192:262 (1991); Hakes et al., *Anal. Biochem.* 202:293 (1992)).

While cleavage by thrombin in the currently known linker sequence region is reasonably specific, it is not absolute. Although thrombin is a reasonably specific enzyme, it can use a variety of different amino acid sequences as its cleavage site. If the target protein contains thrombin cleavage sites, then the cleavage can occur at those sites, resulting in the production of an internally cleaved protein, rather than the desired full length protein.

For example, when *Halobacterium halobium* L11 protein, which contains an internal thrombin cleavage sequence, was expressed as a GST fusion protein that contained the Leu-Val-Pro-Arg-Gly-Ser (SEQ ID NO:1) thrombin cleavage site between the GST tag and L11, treatment with thrombin resulted in cleavage within the target protein L11, and not between L11 and the GST tag (Porse et al., *J. Mol. Biol.* 276:391 (1998)). The Cdc14p protein of *Saccharomyces cerevisiae* also has an internal thrombin cleavage sequence. When the Cdc14p protein was expressed as a GST fusion protein containing a Ser-Gly-Gly-Gly-Gly-Leu-Val-Pro-Arg-Gly-Ser (SEQ ID NO:6) thrombin cleavage site, the fusion protein was cleaved at the internal site within Cdc14p as well as the site within the thrombin cleavage linker (Taylor et al., *J. Biol. Chem.* 272:24054 (1997)).

The present invention provides a novel linker sequence for thrombin cleavage which provides superior specificity to those known in the art.

SUMMARY OF THE INVENTION

The present invention provides a peptide linker comprising a novel thrombin cleavage site, which is useful for the recombinant production of fusion proteins comprising a protein of interest and for separation of the protein of interest from the fusion protein. In one embodiment, the peptide linker comprises the sequence:

X1-X2-Ser-Pro-X3-X4-X5 wherein,

X1 is two or more amino acid residues that are the same or different from each other;

X2 is a hydrophobic amino acid;

X3 is arginine or lysine;

X4 is alanine or glycine; and

X5 is a non-acidic amino acid.

The present invention provides a fusion protein comprising a protein of interest, a fusion partner, and the peptide linker of the present invention interposed there between. The present invention also provides a method of separating a protein of interest from a fusion protein, comprising contacting said fusion protein with a sufficient amount of thrombin such that cleavage of the peptide linker occurs. After the cleavage reaction occurs, the protein of interest is generated from the fusion protein. The protein of interest can be recovered using simple techniques well known to those having ordinary skill in the art.

The present invention may be used to purify any prokaryotic or eukaryotic protein that can be expressed as the product of recombinant DNA technology in a host cell. These recombinant protein products include cytokines, chemokines, hormones, receptors, enzymes, storage proteins, blood proteins, mutant proteins produced by protein engineering techniques, or synthetic proteins.

Additionally, the present invention relates to polynucleotides encoding the peptide linkers, polynucleotides encoding the fusion proteins, vectors containing the same, and host cells containing the vectors.

The present invention further provides methods of preparing a polynucleotide encoding a fusion protein, methods for producing a fusion protein, and methods for producing a protein of interest.

The present invention also provides kits comprising the polynucleotides and vectors of the invention.

BRIEF DESCRIPTION OF THE DRAWINGS

FIG. 2A shows the thrombin cleavage of GST-IL11(A).

FIG. 2B shows the thrombin cleavage of GST-IL11(A).

DETAILED DESCRIPTION OF THE INVENTION

Figure 1:
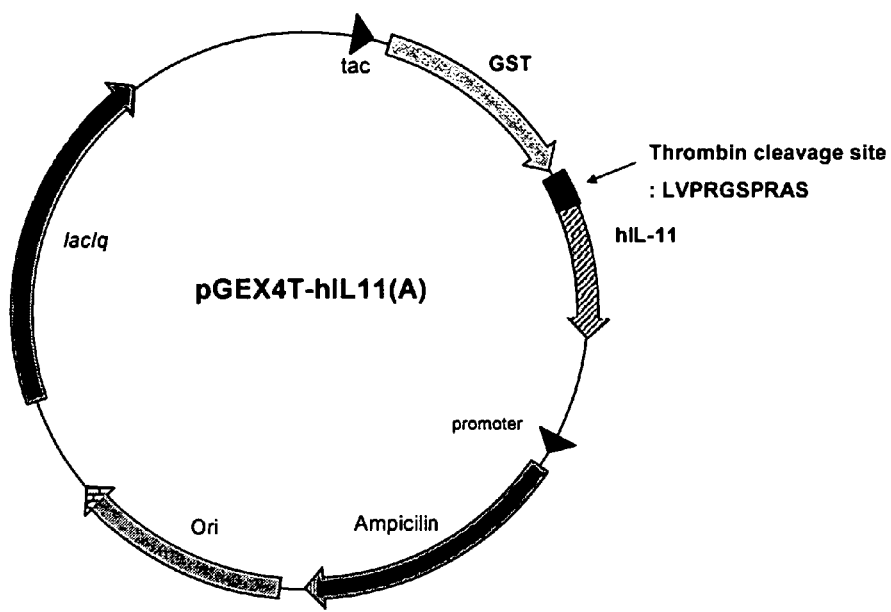
FIG. 1 shows a schematic representation of pGEX4T-hIL11(A) encoding a fusion protein comprising a peptide linker of the invention (SEQ ID NO:8).

The present invention provides a linker peptide comprising a thrombin cleavage site that is cleavable with thrombin and the like. In one embodiment, the peptide linker comprises the sequence:

X1-X2-Ser-Pro-X3-X4-X5 wherein,
X1 is two or more amino acid residues that are the same or different from each other;
X2 is a hydrophobic amino acid;
X3 is arginine or lysine;
X4 is alanine or glycine; and
X5 is a non-acidic amino acid.

In one embodiment, X1 is four or more amino acid residues that are the same or different from each other. In another embodiment, X1 is no more than 10 amino acid residues, e.g., no more than 8 amino acid residues, e.g., no more than 6 amino acid residues. For example, in various embodiments X1 may be 2-6, 2-8, 2-10, 4-6, 4-8, or 4-10 amino acid residues.

When the peptide linker is treated with thrombin, the cleavage occurs at the bond between X3 and X4. Relative to the cleavage site, X1 occupies positions 5 and 6 (P5-P6) when X1 is two amino acid residues or positions 5 to 8 (P5-P8) when X1 is four amino acid residues. X2, Ser, Pro, X3, X4 and X5 each occupies position 4, 3, 2, 1, 1', and 2' (P4, P3, P2, P1, P1', P2'), respectively. In one embodiment, X1 comprises Pro and Arg. In one embodiment, X3 can be Arg or Lys. Thrombin cleaves peptide bonds when either Arg or Lys precedes the carboxyl group. In another embodiment, X4 can be Ala or Gly. The properties of Ala and Gly are very similar, both being small and non polar amino acids. In one embodiment, X2 can be a hydrophobic amino acid selected from the group consisting of Gly, Ala, Pro, Val, Leu, Ile, Met, Phe, Tyr and Trp. In a particular embodiment, X2 is Gly. In a further embodiment, X5 can be a non-acidic amino acid selected from the group consisting of Ser, Ala, Asn, Val, Leu, Ile, Lys, Phe, Tyr and Trp. In a particular embodiment, X5 is Ser. In one embodiment, X1 can be two or more of any amino acid. In another embodiment, X1 can be four or more of any amino acid. The exact amino acid sequence of X1 does not have significant effects on thrombin cleavage.

In one embodiment, the peptide linker comprises the sequence Pro-Arg-Gly-Ser-Pro-Arg↓Ala-Ser (SEQ ID NO:7). In a further embodiment, the peptide linker comprises the sequence Leu-Val-Pro-Arg-Gly-Ser-Pro-Arg↓Ala-Ser (SEQ ID NO:8). When a fusion protein containing this cleavage site is treated with thrombin, the Arg↓Ala bond within the cleavage site is cleaved. In one embodiment, the peptide linker comprises a sequence other than Pro-Arg-Gly-Ser-Pro-Arg↓Ala-Ser (SEQ ID NO:7). In another embodiment, the peptide linker comprises a sequence other than Leu-Val-Pro-Arg-Gly-Ser-Pro-Arg↓Ala-Ser (SEQ ID NO:8).

The peptide linker sequences Pro-Arg-Gly-Ser-Pro-Arg↓Ala-Ser (SEQ ID NO:7) and Leu-Val-Pro-Arg-Gly-Ser-Pro-Arg↓Ala-Ser (SEQ ID NO:8) differ from previously known thrombin cleavage sites because the P3 amino acid Ser is not hydrophobic. According to previous studies, optimum thrombin cleavage sites contain a hydrophobic amino acid at the P3 position (Chang, *Eur. J. Biochem.* 151:217 (1985)). The presence of a non hydrophobic amino acid in the P3 position is known to prolong the time for thrombin cleavage. Raftery et al. reported that the amino acid sequence Asn-Asn-Pro-Arg-Gly-His (SEQ ID NO:9) found in the murine MRP14 protein could be the substrate of thrombin, but it was a poor substrate compared with Leu-Val-Pro-Arg-Gly-Ser (SEQ ID NO:1) (Raftery et al., *Protein Expr. Purif.* 15:228 (1999)). In the case of fibrinogen, which is a natural substrate of thrombin, Gly is located at the P3 position in fibrinopeptides A (Gly-Gly-Val-Arg↓Gly-Pro) (SEQ ID NO:10), while Ser is found at P3 in fibrinopeptides B (Phe-Ser-Ala-Arg↓Gly-His) (SEQ ID NO:11). Fibrinopeptides A is cleaved more rapidly than fibrinopeptides B by thrombin (Binnie et al., *Blood.* 81:3186 (1993)).

The present invention provides a fusion protein comprising a protein of interest, a fusion partner, and the peptide linker of the present invention interposed there between.

The terms "fusion protein" and "chimeric protein," as used herein, are interchangeable and refer to polypeptides and proteins which comprise a protein of interest, a fusion partner and a linker peptide with a thrombin cleavage site interposed there between. In one embodiment, the protein of interest is linked to the N-terminus of the peptide linker and the fusion partner is linked to the C-terminus of the peptide linker. In another embodiment, the protein of interest is linked to the C-terminus of the peptide linker and the fusion partner is linked to the N-terminus of the peptide linker. In a further embodiment, a fusion protein may comprise more than one protein of interest and/or more than one fusion partner, each separated by a peptide linker. In these embodiments, the multiple proteins of interest may be the same or different, the multiple fusion partners may be the same or different, and the multiple peptide linkers may be the same or different.

The terms "protein of interest," "desired polypeptide," "desired protein," or "target protein," as used herein, are interchangeable and refer to any protein or peptide the production of which is desirable. In one embodiment, the protein or peptide is biologically active. Examples of proteins of interest include, but are not limited to, interleukin (IL)-11, thymosin β4, thymosin α1, 1L-2, IL-3, IL-4, IL-5, IL-6, IL-7, IL-8, IL-10, IL-13, IL-15, IL-18, Protease-activated receptor 1 (PAR1), PAR3, PAR4, RANTES, stromal cell-derived factor-1α, monocyte chemotactic protein, stem cell factor, FLT-3L, parathyroid hormone, thrombopoietin, epidermal growth factor, basic fibroblast growth factor, insulin-like growth factor, granulocyte-macrophage colony stimulating factor, granulocyte colony stimulating factor, macrophage colony stimulating factor, platelet-derived growth factor, transforming growth factor (TGF)-β1, tumor necrosis factor (TNF)-α, interferon (IFN)-α, IFN-β, IFN-γ, hepatocyte growth factor, vascular endothelial growth factor and immunoglobulin heavy chain. In one embodiment, the protein of interest is selected from the group consisting of human IL11, thymosin β4, IL-6 and PAR4. In another embodiment, the protein of interest is human IL11.

The term "fusion partner," as used herein, refers to any protein or peptide the inclusion of which in a fusion protein is desirable. In one embodiment, the fusion partner imparts an improved characteristic to the fusion protein, e.g., ease of purification, stability, solubility, and the like. In one embodiment, the fusion partner is an affinity peptide. Examples of affinity peptides include, but are not limited to, glutathione-S-transferase (GST), maltose binding protein (MBP), hexa-histidine, T7 peptide, ubiquitin, Flag peptide, c-myc peptide, polyarginine, polycysteine, polyphenylalanine, BTag, galactose binding domain, cellulose binding domain (CBD), thioredoxin, staphylococcal protein A, streptococcal protein G, calmodulin, beta-galactosidase, chloramphenicol acetyltransferase, S-peptide, streptavidin, His-tag, and Strep-tag.

The term "peptide linker," as used herein, refers to a specific amino acid sequence which comprises a thrombin cleavage site which is recognized and cleaved by thrombin.

The term "thrombin" as used herein, refers to any form of thrombin which is capable of cleaving the peptide linker of the invention. Thrombin may include naturally occurring thrombin, recombinant thrombin, thrombin fragments, and thrombin analogs, as long as some level of cleavage activity is retained by the protein. In one embodiment, thrombin may be human thrombin or bovine thrombin, including naturally occurring thrombin, recombinant thrombin, or thrombin fragments and analogs derived from the human or bovine sequence.

The present invention provides a method of separating a protein of interest from a fusion protein comprising said protein of interest, a fusion partner, and a peptide linker interposed there between, said method comprising contacting said fusion protein with a sufficient amount of thrombin such that cleavage of the peptide linker occurs. In one embodiment, the fusion protein is cleaved between X3 and X4 of the peptide linker. The method may further involve separating the protein of interest from the other portion of the fusion protein, e.g., by affinity purification or size separation.

In one embodiment, the thrombin is human thrombin and the fusion protein is contacted with about 0.1 USP units to about 1.0 USP units of thrombin, e.g., about 0.2 units to about 0.7 units of thrombin, e.g., about 0.2 units to about 0.5 units of thrombin, e.g., about 0.2 units to about 0.3 units of thrombin. In another embodiment, the thrombin is human thrombin and the fusion protein is contacted with thrombin for about 5 minutes to about 1.5 hours, e.g., about 8 minutes to about 1.2 hours, e.g., about 10 minutes to about 1.0 hours. In a further embodiment, the thrombin is human thrombin and the fusion protein is contacted with about 0.25 units of thrombin for about 30 minutes.

In one embodiment, the thrombin is bovine thrombin and the fusion protein is contacted with about 0.1 units to about 1.0 units of thrombin, e.g., about 0.2 units to about 0.7 units of thrombin. In another embodiment, the thrombin is bovine thrombin and the fusion protein is contacted with thrombin for about 5 minutes to about 1.5 hours, e.g., about 8 minutes to about 1.2 hours, e.g., about 10 minutes to about 1.0 hours. In a further embodiment, the thrombin is bovine thrombin and fusion protein is contacted with about 0.5 units of thrombin for about 1.0 hours.

The present invention provides a polynucleotide encoding the peptide linker of the invention. The polynucleotide may be prepared by chemical synthesis or cloning.

The present invention provides a polynucleotide encoding the fusion protein of the invention. In accordance with the present invention, a polynucleotide sequence coding for a protein of interest is isolated, synthesized or otherwise obtained and operably linked to a polynucleotide sequence coding for the linker peptide. The hybrid polynucleotide containing the gene for a desired protein operably linked to a polynucleotide sequence encoding a linker peptide is referred to as a chimeric polynucleotide. In one embodiment, the chimeric polynucleotide is prepared by amplification, e.g., polymerase chain reaction, using primers incorporating the polynucleotide sequence encoding the peptide linker, such that the amplification product comprises the polynucleotide encoding the peptide sequence operably linked to the polynucleotide encoding the protein of interest. In other embodiments, the polynucleotides are ligated together using a ligase. The chimeric polynucleotide is then operably linked to a polynucleotide encoding a fusion partner to produce a polynucleotide encoding the fusion protein. In other embodiments, a polynucleotide encoding a fusion partner is operably linked to a polynucleotide encoding the peptide linker to form a chimeric polynucleotide, and the chimeric polynucleotide is then linked to a polynucleotide encoding a protein of interest to produce a polynucleotide encoding the fusion protein.

The term "operably linked," as used herein to refer to two polynucleotides that encode a protein or peptide, means that the two polynucleotides are linked in such a manner that a continuous open reading frame exists that bridges both polynucleotides. As related to regulatory elements, the term "operably linked" refers to a regulatory element being linked to a polynucleotide encoding a protein or peptide in such a manner that the regulatory element exerts an effect on the transcription and/or translation of the polynucleotide.

The present invention provides a vector (e.g., a plasmid, virus, or bacteriophage vector) comprising a polynucleotide encoding the peptide linker. In one embodiment, the vector is an expression vector. The vector preferably is autonomously replicable in a host cell and preferably contains a selectable marker such as a drug resistance gene (e.g., ampicillin or tetracycline) or an auxotrophy complement gene. In one embodiment, the vector further comprises a polynucleotide encoding a fusion partner operably linked, (e.g., upstream or downstream in the same reading frame) to the polynucleotide encoding the peptide linker. In another embodiment, the vector further comprises a polynucleotide encoding a protein of interest operably linked, (e.g., upstream or downstream in the same reading frame) to the polynucleotide encoding the peptide linker. In another embodiment, the vector comprises a polynucleotide encoding a fusion protein comprising a protein of interest, a fusion partner, and a peptide linker interposed there between. In one embodiment, the vector comprising the polynucleotide encoding the peptide linker further comprises one or more cloning sites, e.g., restriction enzyme recognition sites, upstream and/or downstream of the polynucleotide encoding the peptide linker to facilitate the cloning of polynucleotides encoding proteins of interest or fusion partners into the vector in frame with the peptide linker.

The vector provides the necessary regulatory sequences (e.g., transcription and translation elements) to control expression of the fusion protein in a suitable host cell. The regulatory sequences may include one or more of promoter regions, enhancer regions, transcription termination sites, ribosome binding sites, initiation codons, splice signals, introns, polyadenylation signals, Shine/Dalgarno translation sequences, and Kozak consensus sequences. Regulatory sequences are chosen with regard to the host cell in which the fusion protein is to be produced. Suitable bacterial promoters include, but are not limited to, bacteriophage λ pL or pR, T6, T7, T7/lacO, lac, recA, gal, trp, ara, hut, and trp-lac. Suitable eukaryotic promoters include, but are not limited to, PRBI, GAPDH, metallothionein, thymidine kinase, viral LTR, cytomegalovirus, SV40, or tissue-specific or tumor-specific promoters such as α-fetoprotein, amylase, cathepsin E, M1 muscarinic receptor, or γ-glutamyl transferase.

Fusion proteins which are to be secreted from a host cell into the culture medium or into the periplasm of the host cell may also contain a signal sequence. The signal sequence may be the fusion partner or may be in addition to the fusion partner. A polynucleotide encoding a signal sequence may be operably linked to the 5' end of the polynucleotide encoding the fusion protein. Further, an additional peptide linker may be inserted between the signal sequence and the rest of the fusion protein such that the signal sequence may be removed from the fusion protein by cleavage with thrombin. Suitable signal sequences are well known in the art and include, for example, MBP, GST, TRX, DsbA, and LamB from *E. coli* and α-factor from yeast.

Additional examples of suitable expression vectors are found in U.S. Pat. No. 5,814,503, which is incorporated herein by reference.

The present invention provides a method of preparing a polynucleotide encoding a fusion protein, comprising inserting a polynucleotide encoding a protein of interest into a cloning site of a vector such that the polynucleotide is upstream or downstream and in frame with a polynucleotide encoding the peptide linker. In a further embodiment, the polynucleotide encoding a protein of interest is inserted into a cloning site of a vector comprising a polynucleotide sequence encoding a peptide linker operably linked to a polynucleotide encoding a fusion partner such that the polynucleotide encoding a protein of interest is upstream or downstream and in frame with a polynucleotide encoding the peptide linker.

The present invention provides a host cell comprising a vector of the invention. The host cell may be any cell suitable for expression of fusion proteins, including prokaryotic (e.g., bacterial) and eukaryotic (e.g., fungi, yeast, animal, insect, plant) cells. Suitable prokaryotic host cells include, but are not limited to, *E. coli* (e.g., strains DH5, HB101, JM109, or W3110), *Bacillus, Streptomyces, Salmonella, Serratia*, and *Pseudomonas* species. Suitable eukaryotic host cells include, but are not limited to, COS, CHO, HepG-2, CV-1, LLC-MK$_2$, 3T3, HeLa, RPMI8226, 293, BHK-21, Sf9, *Saccharomyces, Pichia, Hansenula, Kluyveromyces, Aspergillus*, or *Trichoderma* species.

Methods and materials for preparing recombinant vectors and transforming host cells using the same, replicating the vectors in host cells and expressing biologically active foreign polypeptides and proteins are described in Old et al., Principles of Gene Manipulation, 2nd edition, (1981); Sambrook et al., Molecular Cloning, 3rd edition, Cold Spring Harbor Laboratory, 2001, and Ausubel et al., Current Protocols in Molecular Biology, John Wiley & Sons, New York 3rd edition, (2000), each incorporated herein by reference. Vectors may be introduced into a host cell by any means known in the art, including, but not limited to, transformation, calcium phosphate precipitation, electroporation, lipofection, microinjection, and viral infection.

The present invention provides a method for producing a fusion protein, comprising preparing a vector comprising a polynucleotide encoding a fusion protein of the invention, delivering the vector into a host cell, culturing the host cell under conditions in which the fusion protein is expressed, and separating the fusion protein. The method may further comprise contacting the separated fusion protein with thrombin to cleave the fusion protein and separating the protein of interest.

The present invention further provides a method for producing a protein of interest, comprising preparing a vector comprising a polynucleotide encoding a fusion protein of the invention, delivering the vector into a host cell, culturing the host cell under conditions in which the fusion protein is expressed, separating the fusion protein, contacting the separated fusion protein with thrombin to cleave the fusion protein, and separating the protein of interest.

The fusion protein may be separated from the host cell by any means known in the art. If the fusion protein is secreted from the host cell, the culture medium containing the fusion protein may be collected. If the fusion protein is not secreted from the host cell, the cell may be lysed to release the fusion protein. For example, bacterial cells may be lysed by application of high pressure (e.g., with a high pressure homogenizer) or by sonication.

Preferably, the fusion protein is separated by affinity purification based on the fusion partner. For example, a fusion protein comprising GST may be separated on a glutathione-containing column and a fusion protein comprising a hexahistidine tag may be separated on a metal-containing column.

While affinity purification methods are preferred for separation of the fusion protein, any known technique for separating proteins may be used instead of or in addition to affinity purification, including solvent extraction, ultrafiltration, ammonium sulfate fractionation, HPLC, gel filtration chromatography, ion exchange chromatography, hydrophobic interaction chromatography, electrophoresis, and isoelectric focusing.

In one embodiment, the separated fusion protein may be contacted with thrombin and the cleaved protein separated by affinity chromatography such that the fusion partner is bound to the column and the protein of interest passes through and is collected. In another embodiment, the fusion protein may be separated by affinity chromatography and then contacted with thrombin after being eluted from the affinity media. In a further embodiment, the fusion protein may be contacted with thrombin while the fusion protein is still attached to the affinity media, thereby releasing the protein of interest. The concentration of thrombin can range from about 0.1 to about 100 USP units/ml, e.g., about 1 to about 50 units/ml, e.g., about 10 units/ml. Flow rate can be adjusted to 0 ml/min by stopping the pump and then maintained for about 5 to about 60 min, e.g., about 10 to about 15 min.

Conditions for cleavage of the fusion protein by thrombin are well known in the art, and typically are as follows: about pH of about 7 to about 9, about 4° C. to about 37° C., substrate:enzyme ratio of about 5:1 to about 125:1 (molar ratio), for about 1 to about 24 hours.

The protein purification techniques described above may also be used for separation of the protein of interest following cleavage of the fusion protein by thrombin. In one embodiment, the protein of interest is subjected to cation exchange chromatography (e.g., CM SEPHAROSE) and/or an anion exchange chromatography (e.g., Q SEPHAROSE). In one embodiment, the protein of interest is first subjected to cation exchange chromatography, and subsequently subjected to anion exchange chromatography.

For example, recombinant IL-11 protein isolated from affinity chromatography can first be purified using a cation exchange column, e.g., CM Sepharose Fast Flow medium. The column packed with the medium can be equilibrated with Buffer B containing 25 mM Tris-HCl. Sample containing IL-11 protein can be diluted about 4-fold with Buffer B and then loaded onto the column. To wash the column, Buffer B can be loaded and then Buffer E containing 0.15 M Gly-NaOH, pH 9.5 can be applied. Target protein can be eluted with Buffer F containing 0.15 M Gly-NaOH, pH 9.5 and 0.15 M NaCl. All procedures of this step may be performed at about 4° C. The pH value of Buffer B can range from about 7.5 to about 8.5. In the cases of Buffer E and Buffer F, pH can range from about 9.2 to about 9.7.

Recombinant IL-11 protein eluted from the cation exchange column can be further purified using an anion exchange column, e.g., Q Sepharose Fast Flow medium. The column packed with this medium can be equilibrated with Buffer G containing 1 M Gly-NaOH, pH 9.5. This column is re-equilibrated with Buffer H containing 40 mM Gly-NaOH, pH 9.5. Sample obtained from the previous step can be diluted about 4-fold with water and then loaded onto the column. Flow-through containing the target protein can then be collected. Buffer H containing 40 mM Gly-NaOH, pH 9.5 is applied to the column and the flow-through is also collected. The pH value during this step can range from about 9.2 to about 9.7 or about 9.5. All procedures of this anion exchange chromatography may be performed at about room temperature. Endotoxin can be efficiently eliminated through these procedures.

The invention provides a kit comprising a polynucleotide encoding a peptide linker. In one embodiment, the kit comprises a vector comprising the polynucleotide encoding a peptide linker. In another embodiment, the vector is an expression vector. In one embodiment, the vector further comprises a polynucleotide encoding a fusion partner operably linked, e.g., upstream or downstream in the same reading frame, to the polynucleotide encoding the peptide linker. In another embodiment, the vector further comprises a polynucleotide encoding a protein of interest operably linked, e.g., upstream or downstream in the same reading frame, to the polynucleotide encoding the peptide linker. In another embodiment, the vector comprises a polynucleotide encoding a fusion protein comprising a protein of interest, a fusion partner, and a peptide linker interposed there between. In one embodiment, the vector comprising the polynucleotide encoding the peptide linker further comprises one or more cloning sites, e.g., restriction enzyme recognition sites, upstream and/or downstream of the polynucleotide encoding the peptide linker to facilitate the cloning of polynucleotides encoding proteins of interest or fusion partners into the vector in frame with the peptide linker. In an additional embodiment, the vector comprises the polynucleotide encoding the peptide linker, operably linked to a polynucleotide encoding a fusion partner, and further comprising one or more cloning sites upstream or downstream of the polynucleotide encoding the peptide linker. In one embodiment, the order of the polynucleotides is fusion partner, peptide linker, cloning sites. In an alternative embodiment, the order of the polynucleotides is cloning site, peptide linker, fusion partner. In one embodiment, the kit comprises multiple vectors in which each vector comprises a polynucleotide encoding the peptide linker and multiple cloning sites in a different reading frame relative to the peptide linker, such that a polynucleotide encoding a protein of interest can be inserted into one of the vectors in frame with the peptide linker.

The kit may further comprise other agents related to the use of the vectors, e.g., buffers, restriction enzymes, ligases, phosphorylases, host cells, and the like. The kit may also comprise instructions for use of the vectors, e.g., for insertion of a polynucleotide encoding a protein of interest or production of a fusion protein.

The following examples are illustrative, but not limiting, of the methods of the present invention. Other suitable modifications and adaptations of the variety of conditions and parameters normally encountered in medical treatment and pharmaceutical science and which are obvious to those skilled in the art are within the spirit and scope of the invention.

EXAMPLE 1

GST-IL11(A)

In the present example, GST-IL11(A) fusion protein was prepared. GST-IL11(A) fusion protein is composed of glutathione S-transferase (GST) and human IL-11 with a thrombin cleavage site inserted there between. The thrombin cleavage site for GST-IL11(A) is Leu-Val-Pro-Arg-Gly-Ser-Pro-Arg↓Ala-Ser (SEQ ID NO:8).

To produce GST-IL11(A), an *E. coli* expression plasmid, pGEX4T-hIL11(A), was constructed (FIG. 1). The DNA sequence encoding human IL-11(A) was obtained by PCR and site-directed mutagenesis from human IL-11 cDNA. The following primer pairs were used for PCR.

5': GGA TCC CCG CGA GCT TCC CCA GAC CCT (SEQ ID NO:12) BamHI

3': GTC GAC CCC TTA TCA CAG CCG AGT CTT CAG (SEQ ID NO:13) SalI

The following primer pairs were used for site-directed mutagenesis.

5'DN: CCA GCC ACC CCC GAA CCC GCC GGC GCC (SEQ ID NO:14)

3'DN: GGC GCC GGC GGG TTC GGG GGT GGC TGG (SEQ ID NO:15)

The 5' primer for PCR was designed to encode Pro-Arg-Ala-Ser (SEQ ID NO:16) residues. The BamHI/SalI treated DNA fragment was cloned into the BamHI/SalI site of pGEX4T-1 plasmid, generating pGEX4T-hIL11(A). The plasmid pGEX4T-1 originally has the thrombin cleavage site Leu-Val-Pro-Arg-Gly-Ser (SEQ ID NO:1) behind the GST tag. Therefore, pGEX4T-hIL11(A) has the new thrombin cleavage site Leu-Val-Pro-Arg-Gly-Ser-Pro-Arg↓Ala-Ser (SEQ ID NO:8) between glutathione S-transferase and human IL-11 sequences.

The site-directed mutagenesis was performed to change the Asp155 of wild-type IL-11 (NCBI Accession No.: AAA59132) to Asn.

The amino acid sequence of the hIL11(A) including the thrombin cleavage site is given below:
Leu-Val-Pro-Arg-Gly-Ser-Pro-Arg↓-Ala-Ser-Pro-Asp-Pro-Arg-Ala-Glu-Leu-Asp-Ser -Thr-Val-Leu-Leu-Thr-Arg-Ser-Leu-Leu-Ala-Asp-Thr-Arg-Gln-Leu-Ala-Ala-Gln-Leu -Arg-Asp-Lys-Phe-Pro-Ala-Asp-Gly-Asp-His-Asn-Leu-Asp-Ser-Leu-Pro-Thr-Leu-Ala -Met-Ser-Ala-Gly-Ala-Leu-Gly-Ala-Leu-Gln-Leu-Pro-Gly-Val-Leu-Thr-Arg-Leu-Arg -Ala-Asp-Leu-Leu-Ser-Tyr-Leu-Arg-His-Val-Gln-Trp-Leu-Arg-Arg-Ala-Gly-Gly-Ser -Ser-Leu-Lys-Thr-Leu-Glu-Pro-Glu-Leu-Gly-Thr-Leu-Gln-Ala-Arg-Leu-Asp-Arg-Leu -Leu-Arg-Arg-Leu-Gln-Leu-Leu-Met-Ser-Arg-Leu-Ala-Leu-Pro-Gln-Pro-Pro-Pro-Asn -Pro-Pro-Ala-Pro-Pro-Leu-Ala-Pro-Pro-Ser-Ala-Trp-Gly-Gly-Ile-Arg-Ala-Ala -His-Ala-Ile-Leu--Gly-Gly-Leu-His-Leu-Thr-Leu-Asp-Trp-Ala-Val-Arg-Gly-Leu-Leu -Leu-Leu-Lys-Thr-Arg-Leu (SEQ ID NO:17)

The expression plasmid pGEX4T-hIL11(A) was transformed into *E. Coli* BL21. Transformants were inoculated in LB Broth supplemented with ampicillin (50 μg/ml final concentration), and incubated at 37° C. until OD 600 reached 0.5. Then, isopropyl-β-D-thiogalactopyranoside (IPTG) was added to a final concentration of 0.4 mM to induce protein expression and the cells were grown for an additional 3 h at 37° C. The expression of GST-IL11 was confirmed by SDS-PAGE. The cells were harvested by centrifugation, resuspended in 50 mM Tris-HCl buffer, pH 8.0 and lysed by sonication. Ammonium sulfate was added at a final concentration of 5.6% while maintaining pH 8.0 with Tris powder. Addition of ammonium sulfate was carried out at 4° C. The supernatant containing target protein was applied to a Glutathione Sepharose 4 Fast Flow (Amersham Biosciences) affinity column pre-equilibrated with 25 mM Tris-HC1 buffer, pH 8.0. Following several washes, the bound fusion protein was eluted with 25 mM Tris-HCl buffer containing 150 mM NaCl and 10 mM reduced glutathione, pH 8.0.

The purified fusion protein was digested with thrombin. One hundred micrograms of protein samples were subjected to cleavage by 0.1 units, 0.25 units or 0.5 units of bovine or human thrombin in 25 mM Tris-HCl buffer containing 150 mM NaCl, pH 8, at 20° C. Aliquots were removed from each reaction at various time points (10 min, 30 min, 1 h, 2 h, and 5 h after reaction), and heat-inactivated by boiling for 5 min to stop the reaction. The results were analyzed by SDS-PAGE, and visualized by staining with Coomassie brilliant blue. The fusion protein GST-hIL11(A) gradually split into two major products, the GST fusion partner (26 kDa) and IL-11 (18.2 kDa) as the reaction progressed (FIGS. 2A and 2B), and internal cleavage within IL-11 was not observed. The GST fusion partner was efficiently cleaved by both bovine and human thrombin in the concentration ranges and the time points tested (FIGS. 2A and 2B).

Following cleavage with thrombin, the IL-11 was re-chromatographed using Glutathione Sepharose 4 Fast Flow to remove the GST portion of the fusion protein. The N-terminal amino acid sequence of the IL-11 was analyzed using a Procise 491A HT protein sequencer (Applied Biosystems, USA). It was confirmed that the isolated IL11(A) has the sequence Ala-Ser-Pro-Asp-Pro-Arg-Ala-Glu-Leu-Asp-Ser-Thr-Val-Leu -Leu (SEQ ID NO:42) at its N-terminus.

Alternatively, the GST portion of the fusion protein was removed while the fusion protein was bound on the column containing Glutathione Sepharose 4 Fast Flow medium whose binding capacity is about 10 mg per ml. The column was packed with the Glutathione Sepharose 4 Fast Flow medium, and equilibrated with about 5 times column volume (CV) of Buffer B containing 25 mM Tris-HCl, pH 8.0. After loading of supernatant obtained from bacterial lysate, the column was washed with about 20 CV of Buffer B, and then equilibrated with about 5 CV of Buffer C containing 25 mM Tris-HCl, pH 8.0, and 0.15 M NaCl. Thrombin dissolved in Buffer C was then applied at about 10 units per ml of the medium (or about 1 unit per mg of the binding capacity of the medium). Subsequently, about 3 CV of Buffer C was applied to the column and IL11(A) detached from the fusion partner was collected. All procedures were performed at room temperature, about 20-25° C.

Figure 3:
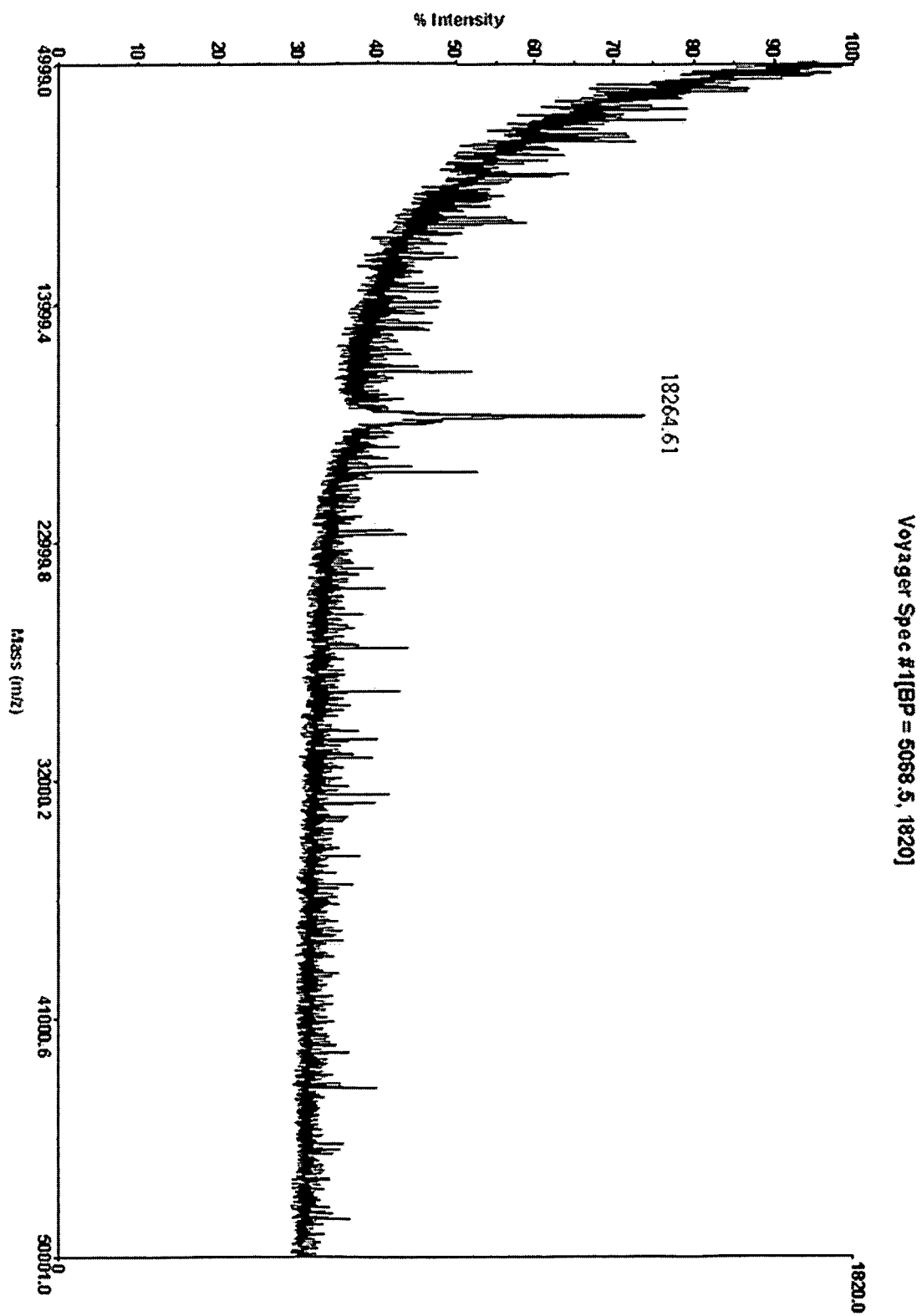
FIG. 3 shows the analysis of IL-11(A) by MALDI-TOF.

To check whether any internal cleavage within IL-11 occurred, IL-11 was further purified by cation exchange chromatography which was followed by anion chromatography, and analyzed by Matrix-Assisted Laser Desorption Ionization Mass Spectrometer (MALDI-TOF/MS) (Proteomics Solution I (Voyager-DE STR), Applied Biosystems). The expected molecular weight of IL-11 was 18.26 kDa according to Compute pI/MW tool (available at au.expasy.org/tools/pi_tool.html), and an 18264 Da peak was observed (FIG. 3). From this result, it was confirmed that intact IL-11 protein was generated after thrombin cleavage of GST-IL11(A).

More specifically, recombinant IL-11 protein isolated from affinity chromatography was first purified using CM Sepharose Fast Flow medium. The column packed with the medium was equilibrated with Buffer B. Sample containing IL-11 protein was diluted about 4-fold with Buffer B and then loaded onto the column. To wash the column, Buffer B was loaded and then Buffer E containing 0.15 M Gly-NaOH, pH 9.5 was applied. Target protein was eluted with Buffer F containing 0.15 M Gly-NaOH, pH 9.5 and 0.15 M NaCl. All procedures of this step were performed at about 4° C.

Recombinant IL-11 protein eluted from the cation exchange column was then further purified using Q Sepharose Fast Flow medium. The column packed with this medium was equilibrated with Buffer G containing 1 M Gly-NaOH, pH 9.5. This column was re-equilibrated with Buffer H containing 40 mM Gly-NaOH, pH 9.5. Sample obtained from the previous step was diluted about 4-fold with water and then loaded onto the column. Flow-through containing the target protein was then collected. Buffer H containing 40 mM Gly-NaOH, pH 9.5 was applied to the column and the flow-through was also collected. The pH value during this step was about 9.5. All procedures of this anion exchange chromatography were performed at about room temperature. Endotoxin was efficiently eliminated through these procedures.

The GST-IL11(A) fusion protein contains the new thrombin cleavage sequence Leu-Val-Pro-Arg-Gly-Ser-Pro-Arg-Ala-Ser (SEQ ID NO:8). Although the Leu-Val-Pro-Arg-Gly-Ser-Pro-Arg-Ala-Ser (SEQ ID NO:8) sequence includes the previously known Leu-Val-Pro-Arg-Gly-Ser (SEQ ID NO:1) sequence, thrombin cleavage occurs not at Arg↓Gly but at Arg↓Ala. It proves that thrombin prefers Leu-Val-Pro- Arg-Gly-Ser-Pro-Arg-Ala-Ser (SEQ ID NO:8) to Leu-Val-Pro-Arg-Gly-Ser (SEQ ID NO:1).

EXAMPLE 2

GST-Thymosin β4

Figure 4:
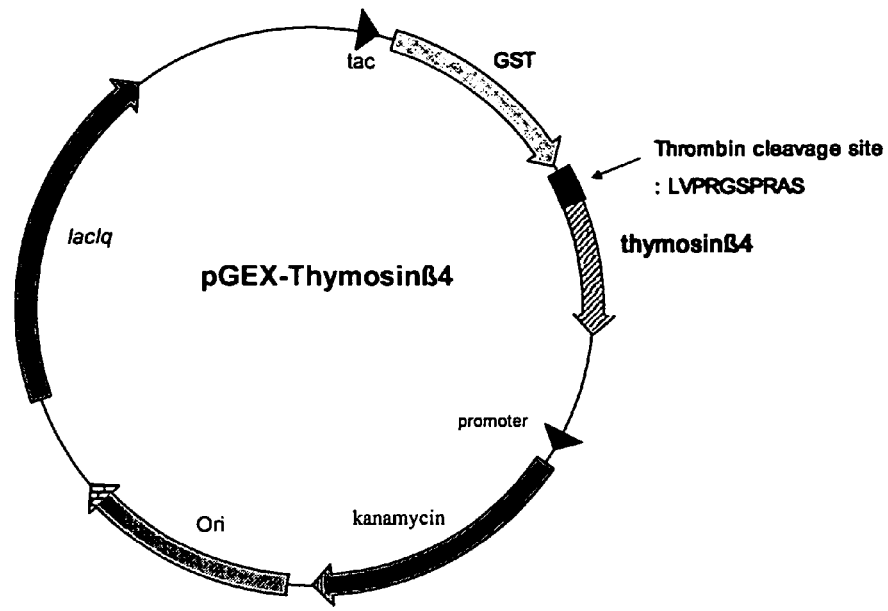
FIG. 4 shows the schematic representation of pGEX-Thymosinβ4 encoding a fusion protein comprising a peptide linker of the invention (SEQ ID NO:8).

The GST-Thymosin β4 expression plasmid, pGEX-Thymosin β4, was constructed by inserting a cDNA of thymosin β4 into pGEX4T-1-Kan (FIG. 4). A cDNA encoding human thymosin β4 was cloned from total RNA prepared from K562 cells by reverse transcription (RT)-polymerase chain reaction (PCR). The oligonucleotide sequences for PCR were as follows:

5': GGATCCCCTCGAGCTTCTGACAAAC-CCGATATG(SEQ ID NO:18) BamHI
3': GTCGACTTTACGATTCGCCTGCTTGCTTCTC (SEQ ID NO:19) SalI

The 5' primer was designed to contain the coding sequence for Gly-Ser-Pro-Arg↓Ala-Ser (SEQ ID NO:20), so that the Leu-Val-Pro-Arg-Gly-Ser-Pro-Arg↓Ala-Ser (SEQ ID NO:8) sequence could be generated when the PCR product was cloned into pGEX4T-1 expression plasmid.

A 135 bp cDNA product was generated by the PCR. The amplified product was cloned into the pGEM-T Easy plasmid (Promega, Wis., USA), resulting in pGEM-Thymosin β4. Following sequence confirmation, the BamHI/SalI fragment of pGEM-Thymosin β4 was cloned into the corresponding sites of the pGEX4T-1-Kan vector which was prepared from pGEX4T-1 by replacing the ampicillin resistance gene with the kanamycin resistance gene.

The amino acid sequence of thymosin β4 including the thrombin cleavage site is given below.
Leu-Val-Pro-Arg-Gly-Ser-Pro-Arg↓-Ala-Ser-Asp-Lys-Pro-Asp-Met-Ala -Glu-Ile-Glu-Lys-Phe-Asp-Lys-Ser-Lys-Lys-Thr-Glu-Thr-Gln-Glu -Glu-Ser(SEQ ID NO:21)

The expression plasmids were transformed into *E. coli* DH5α. Transformants were inoculated in LB Broth, and incubated at 37° C. until OD 600 reached 0.5, and IPTG was added to a final concentration of 0.4 mM. Incubation was continued for 3 h, and the cells were harvested by centrifugation. The expression of GST-Thymosin β4 was confirmed by SDS-PAGE. The bacterial pellets were resuspended in 50 mM Tris-HCl buffer, pH 8.0 buffer and lysed by sonication. GST-Thymosin β4 was purified by Glutathione Sepharose 4 Fast Flow from the soluble fraction.

Figure 5:
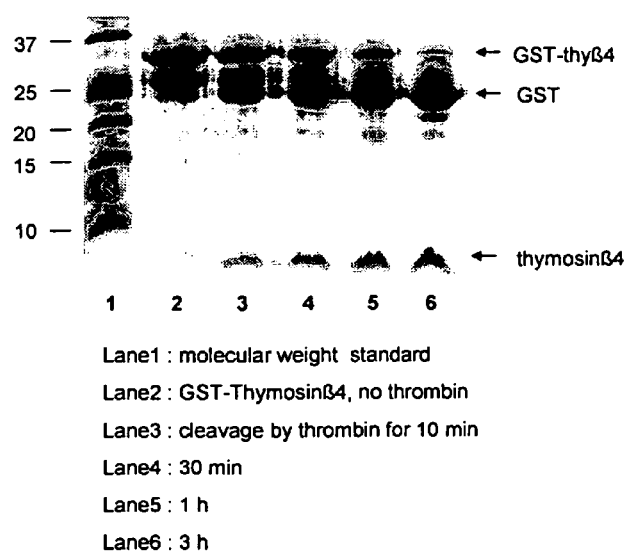
FIG. 5 shows the thrombin cleavage of GST-Thymosinβ4.

The purified fusion proteins were digested with thrombin and analyzed by SDS-PAGE using 15% tricine separation gel. One hundred micrograms of protein samples were subjected to cleavage by 0.5 units thrombin in 25 mM Tris-HCl buffer, pH 8.0 containing 150 mM NaCl, and 10 mM reduced glutathione, at 20° C. Aliquots were removed from each reaction at various time points (10 min, 30 min, 1 h, and 3 h after reaction), and heat-inactivated by boiling for 5 min to stop the reaction. The fusion protein GST-Thymosin β4 (31 kDa) gradually disappeared, and the amount of thymosin β4 (5 kDa) increased as reaction time passed (FIG. 5).

Following cleavage with thrombin, the thymosin β4 was re-chromatographed using Glutathione Sepharose 4 Fast Flow to remove the GST portion of the fusion protein. The N-terminal amino acid sequence of the thymosin β4 was analyzed using a Procise 491A HT protein sequencer (Applied Biosystems, USA). It was confirmed that the isolated thymosin β4 has the sequence Ala-Ser-Asp-Lys-Pro-Asp-Met-Ala-Glu-Ile (SEQ ID NO:22) at its N-terminus.

Figure 6:
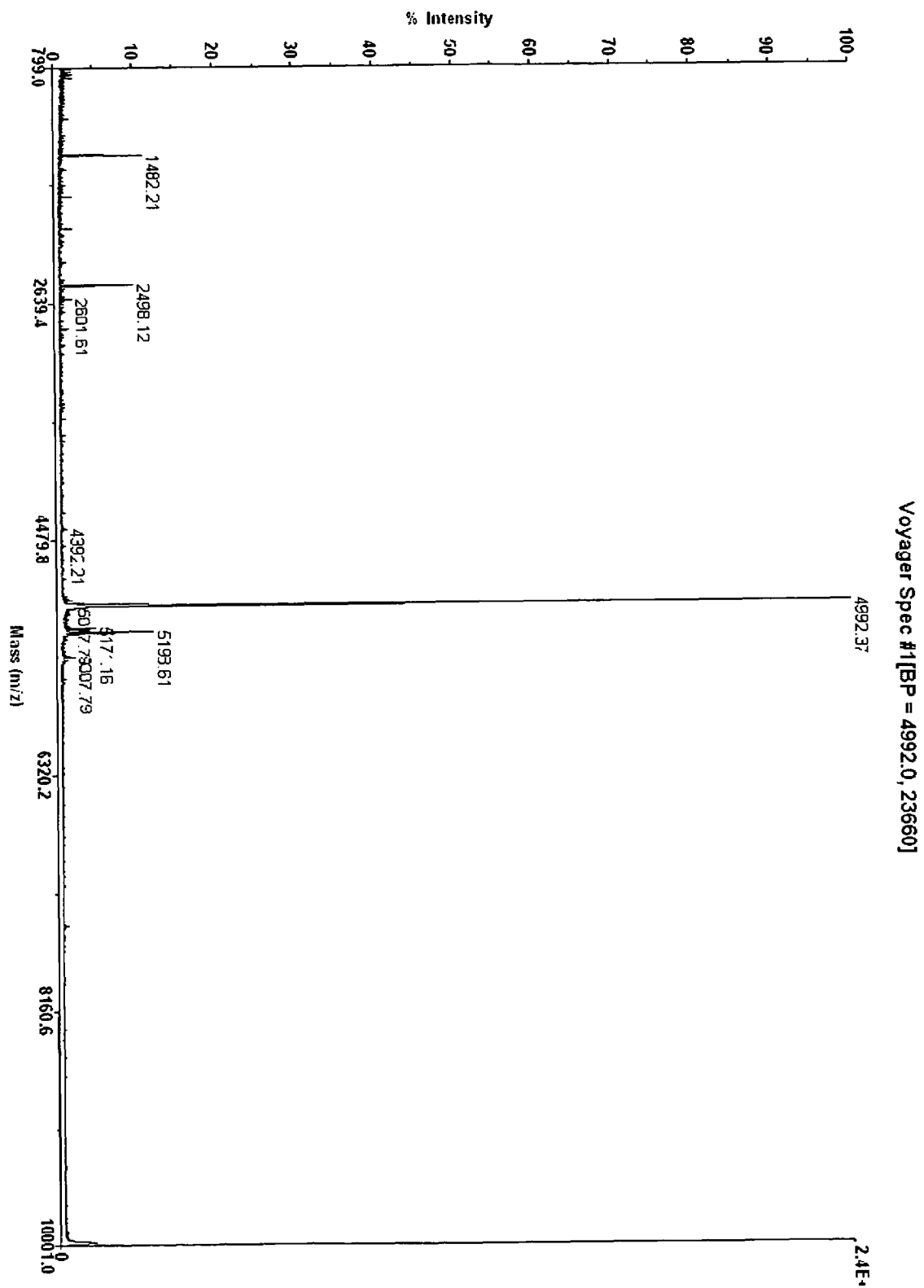
FIG. 6 shows the analysis of thymosin β4 by MALDI-TOF.

To check whether any internal cleavage within thymosin β4 occurred, thymosin β4 was further purified by cation exchange chromatography and anion chromatography, and analyzed by MALDI-TOF/MS (Proteomics Solution I (Voyager-DE STR), Applied Biosystems). The expected molecular weight of thymosin β4 was 5.02 kDa according to Compute pI/MW tool (available at au.expasy.org/tools/pi_tool.html), and a 4992 Da peak was observed (FIG. 6). From this result, it was confirmed that intact thymosin β4 protein was generated after thrombin cleavage of GST-Thymosin β4.

EXAMPLE 3

GST-IL6

Figure 7:
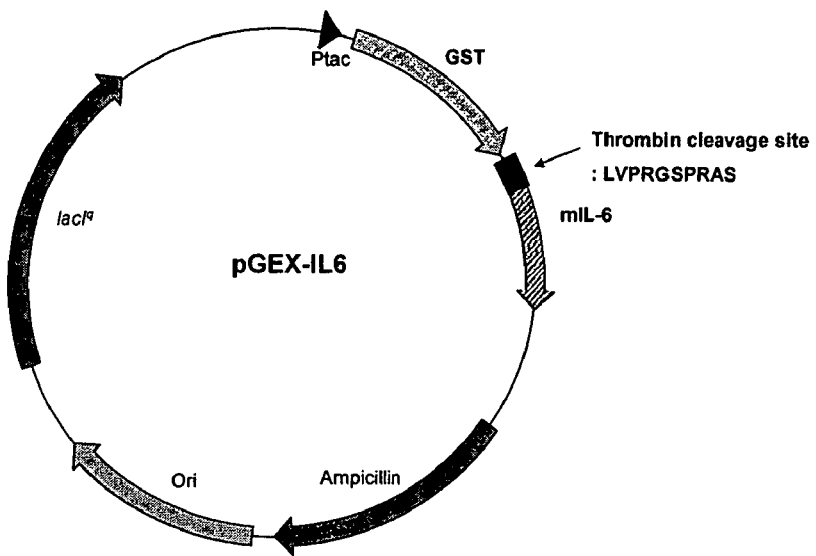
FIG. 7 shows the schematic representation of pGEX-IL6 encoding a fusion protein comprising a peptide linker of the invention (SEQ ID NO:8).

The GST-IL6 expression plasmid, pGEX-IL6, was constructed by inserting a cDNA of murine IL-6 into pGEX4T-1 (FIG. 7). A cDNA encoding murine IL-6 was cloned from total RNA prepared from mouse dendritic cells by RT-PCR. The oligonucleotide sequences for PCR were as follows:

5': GGA TCC CCT CGA GCT TCT TTC CCT ACTTCA (SEQ ID NO:23) BamHI
3': GTC GAC CTA GGT TTG CCG AGT AGA TCT (SEQ ID NO:24) SalI

The 5' primer was designed to contain the coding sequence for Gly-Ser-Pro-Arg↓Ala-Ser (SEQ ID NO:20), so that the Leu-Val-Pro-Arg-Gly-Ser-Pro-Arg↓Ala-Ser (SEQ ID NO:8) sequence could be generated when the PCR product was cloned into pGEX4T-1 expression plasmid.

A 588 bp cDNA product was generated by the PCR. The amplified product was cloned into the pGEM-T Easy plasmid, resulting in pGEM-IL6. Following sequence confirmation, the BamHI/SalI fragment of pGEM-IL6 was cloned into the corresponding sites of the pGEX4T-1 vector.

The amino acid sequence of IL-6 including the thrombin cleavage site is given below.
Leu-Val-Pro-Arg-Gly-Ser-Pro-Arg↓-Ala-Ser-Phe-Pro-Thr-Ser-Gln-Val-Arg -Arg-Gly-Asp-Phe-Thr-Glu-Asp-Thr-Thr-Pro-Asn-Arg-Pro-Val-Tyr-Thr-Thr-Ser-Gln -Val-Gly-Gly-Leu-Ile-Thr-His-Val-Leu-Trp-Glu-Ile-Val-Glu-Met-Arg-Lys-Glu -Leu-Cys-Asn-Gly-Asn-Ser-Asp-Cys-Met-Asn-Asn-Asp-Asp-Ala-Leu-Ala-Glu-Asn -Asn-Leu-Lys-Leu-Pro-Glu-Ile-Gln-Arg-Asn-Asp-Gly-Cys-Tyr-Gln-Thr-Gly-Tyr -Asn-Gln-Glu-Ile-Cys-Leu-Leu-Lys-Ile-Ser-Ser-Gly-Leu-Leu-Glu-Tyr-His-Ser -Tyr-Leu-Glu-Tyr-Met-Lys-Asn-Asn-Leu-Lys-Asp-Asn-Lys-Lys-Asp-Lys-Ala-Arg-Val -Leu-Gln-Arg-Asp-Thr-Glu-Thr-Leu-Ile-His-Ile-Phe-Asn-Gln-Glu-Val-Lys-Asp -Leu-His-Lys-Ile-Val-Leu-Pro-Thr-Pro-Ile-Ser-Asn-Ala-Leu-Leu-Thr-Asp-Lys -Leu-Glu-Ser-Gln-Lys-Glu-Trp-Leu-Arg-Thr-Lys-Thr-Ile-Gln-Phe-Ile-Leu-Lys -Ser-Leu-Glu-Glu-Phe-Leu-Lys-Val-Thr-Leu-Arg-Ser-Thr-Arg-Gln-Thr (SEQ ID NO:25)

The expression plasmid was transformed into *E. coli* BL21. Transformants were inoculated in LB Broth supplemented with ampicillin (50 µg/ml final concentration), and incubated at 37° C. until OD 600 reached 0.5, and IPTG was added to a final concentration of 0.4 mM. Incubation was continued for 3 h, and the cells were harvested by centrifugation. The expression of GST-IL6 was confirmed by SDS-PAGE. The bacterial pellets were resuspended in 50 mM Tris-HCl buffer, pH 8.0 and lysed by sonication. GST-IL6 was purified by Glutathione Sepharose 4 Fast Flow from the soluble fraction.

Figure 8:
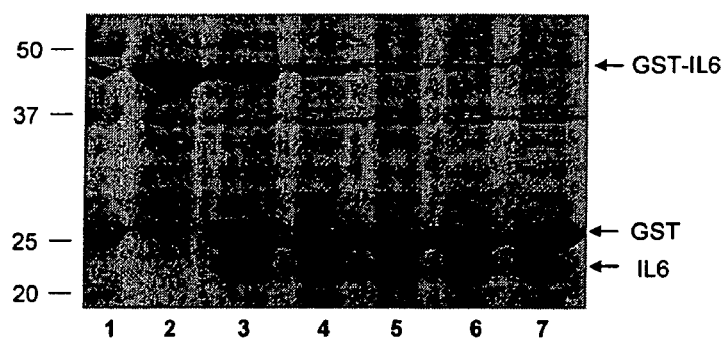
FIG. 8 shows the thrombin cleavage of GST-IL6.

The purified fusion proteins were digested with thrombin and analyzed by SDS-PAGE. One hundred micrograms of protein samples were subjected to cleavage by 0.5 units thrombin in 25 mM Tris-HCl buffer, pH 8.0 containing 150 mM NaCl, and 10 mM reduced glutathione, at 20° C. Aliquots were removed from each reaction at various time points (10 min, 30 min, 1 h, 2 h, and 3 h after reaction), and heat-inactivated by boiling for 5 min to stop the reaction. The fusion protein GST-IL6 (46 kDa) gradually disappeared, and the amount of IL-6 (22 kDa) increased as reaction time passed (FIG. 8).

To check where the cleavage occurred by thrombin treatment, the protein band containing IL-6 protein was obtained, and subjected to amino acid sequencing. First, the purified GST-IL6 protein was treated with thrombin for 3 h, and separated by SDS-PAGE. Then, the proteins in the polyacrylamide gel were transferred to PVDF membrane. After the band containing IL-6 protein was identified, it was sliced away from the PVDF membrane, and subjected to amino acid sequencing. It was confirmed that the IL-6 has the sequence Ala-Ser-Phe-Pro-Thr-Ser-Gln-Val-Arg-Arg (SEQ ID NO:26) at its N-terminus.

EXAMPLE 4

GST-PAR4

The protease-activated receptors (PARs) are known to be activated by the proteolysis of an N-terminal exodomain (Kahn et al., *J. Clin. Invest.* 103:879 (1999)). There are four PARs (PAR1-4) that make up this family of proteins, and PAR 1, 3 and 4 are activated by thrombin (Coughlin, *Proc. Natl. Acad. Sci. USA* 96:11023 (1999)). The amino acid sequence of the thrombin cleavage site on PAR4 is Leu$^{43}$-Pro-Ala-Pro-Arg↓-Gly-Tyr (SEQ ID NO:27). We produced the GST-PAR4 protein which contains Leu-Val-Pro-Arg-Gly-Ser-Pro-Arg↓-Ala-Ser (SEQ ID NO:8) sequence as another thrombin cleavage site to test which site is preferred by thrombin.

Figure 9:
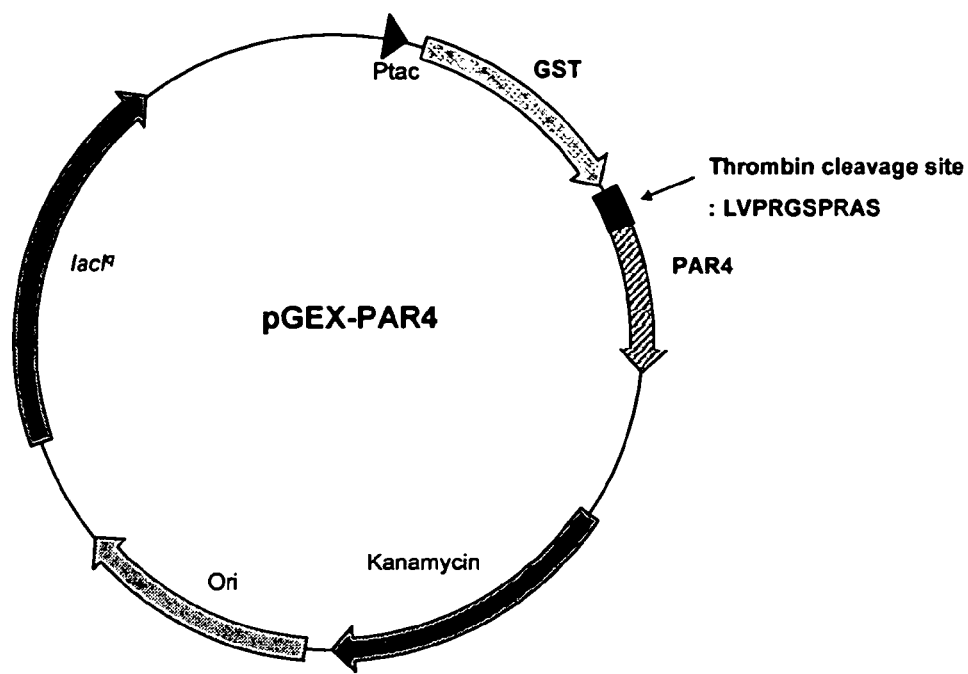
FIG. 9 shows the schematic representation of pGEX-PAR4 encoding a fusion protein comprising a peptide linker of the invention (SEQ ID NO:8)

The GST-PAR4 expression plasmid, pGEX-PAR4, was constructed by inserting a cDNA of human PAR4 into pGEX4T-1-Kan (FIG. 9). A cDNA encoding human PAR4 was cloned from total RNA prepared from K562 cells by RT-PCR. The oligonucleotide sequences for PCR were as follows:

5': GGATCC CCT CGA GCT TCT ATG TGG GGG CGA (SEQ ID NO:28) BamHI
3': GTCGAC TCA GTG CAC CAG GGC CAG GTA (SEQ ID NO:29) SalI

The 5' primer was designed to contain the coding sequence for Gly-Ser-Pro-Arg↓Ala-Ser (SEQ ID NO:20), so that the Leu-Val-Pro-Arg-Gly-Ser-Pro-Arg↓Ala-Ser (SEQ ID NO:8) sequence could be generated when the PCR product was cloned into pGEX4T-1-Kan plasmid.

A 540 bp cDNA product was generated by the PCR. The amplified product was cloned into the pGEM-T Easy plasmid, resulting in pGEM-PAR4. Following sequence confirmation, the BamHI/SalI fragment of pGEM-PAR4 was cloned into the corresponding sites of the pGEX4T-1-Kan vector.

The amino acid sequence of PAR4 including the thrombin cleavage site is given below.

Leu-Val-Pro-Arg-Gly-Ser-Pro-Arg↓-Ala-Ser-Met-Trp-Gly-Arg-Leu-Leu -Leu-Trp-Pro-Leu-Val-Leu-Gly-Phe-Ser-Leu-Ser-Gly-Gly-Thr-Gln-Thr-Pro -Ser-Val-Tyr-Asp-Glu-Ser-Gly-Ser-Thr-Gly-Gly-Gly-Asp-Asp-Ser-Thr-Pro -Ser-Ile-Leu-Pro-Ala-Pro-Arg-Gly-Tyr-Pro-Gly-Gln-Val-Cys-Ala-Asn-Asp -Ser-Asp-Thr-Leu-Glu-Leu-Pro-Asp-Ser-Ser-Arg-Ala-Leu-Leu-Leu-Gly-Tyr -Vla-Pro-Thr-Arg-Leu-Val-Pro-Ala-Leu-Tyr-Gly-Leu-Val-Leu-Val-Val-Gly -Leu-Pro-Ala-Asn-Gly-Leu-Ala-Leu-Trp-Val-Leu-Ala-Thr-Gln-Ala-Pro-Arg -Leu-Pro-Ser-Thr-Met-Leu-Leu-Met-Asn-Leu-Ala-Thr-Ala-Asp-Leu-Leu-Leu -Ala-Leu-Ala-Leu-Pro-Pro-Arg-Ile-Ala-Tyr-His-Leu-Arg-Gly-Gln-Arg-Tyr -Pro-Phe-Gly-Glu-Ala-Ala-Cys-Arg-Leu-Ala-Thr-Ala-Ala-Leu-Tyr-Gly-His -Met-Tyr-Gly-Ser-Val-Leu-Leu-Leu-Ala-Ala-Val-Ser-Leu-Asp-Arg-Tyr-Leu -Ala-Leu-Val-His(SEQ ID NO:30)

The internal thrombin cleavage site is underlined.

The expression plasmid is transformed into *E. coli* BL21. Transformants are inoculated in LB Broth supplemented with kanamycin (50 µg/ml final concentration), and incubated at 37° C. until OD 600 reaches 0.5, and IPTG is added to a final concentration of 0.4 mM. Incubation is continued for 3 h, and the cells are harvested by centrifugation. The expression of GST-PAR4 is confirmed by SDS-PAGE. The bacterial pellets are resuspended in 50 mM Tris-HCl buffer, pH 8.0 and lysed by sonication. GST-PAR4 is purified by Glutathione Sepharose 4 Fast Flow from the soluble fraction.

The purified fusion proteins are digested with thrombin and analyzed by SDS-PAGE. One hundred micrograms of protein samples are subjected to cleavage by 0.5 units thrombin in 25 mM Tris-HCl buffer, pH 8.0 containing 150 mM NaCl, and 10 mM reduced glutathione, at 20° C. Aliquots are removed from each reaction at various time points (10 min, 30 min, 1 h, 2 h, and 3 h after reaction), and heat-inactivated by boiling for 5 min to stop the reaction.

EXAMPLE 5

GST-IL11(LV-)

To test whether the whole Leu-Val-Pro-Arg-Gly-Ser-Pro-Arg-Ala-Ser (SEQ ID NO:8) sequence is required for efficient thrombin cleavage, an expression plasmid encoding Pro-Arg-Gly-Ser-Pro-Arg-Ala-Ser (SEQ ID NO:7) as a thrombin cleavage site was constructed. First, the BamHI/SalI fragment containing IL-11(A) was obtained from pGEX4T-IL11(A) which was described in EXAMPLE 1. Then, it was inserted into the BamHI/SalI site of pGEX6P-2, resulting in pGEX6P-IL11. The plasmid pGEX6P-2 contains "Pro-Leu" sequence upstream of the BamHI site. Therefore, pGEX6P-IL11 can have Pro-Leu-Gly-Ser-Pro-Arg-Ala-Ser (SEQ ID NO:31) because the BamHI/SalI fragment containing IL-11(A) starts as Gly-Ser-Pro-Arg-Ala-Ser (SEQ ID NO:20) sequence. The second amino acid Leu was changed to Arg by site-directed mutagenesis to produce Pro-Arg-Gly-Ser-Pro-Arg-Ala-Ser (SEQ ID NO:7) sequence. The following oligonucleotides were used for the site-directed mutagenesis:

5': CAG GGG CCC CGG GGA TCC CCT CGA GCT (SEQ ID NO:32)
3': AGC TCG AGG GGA TCC CCG GGG CTG (seq ID NO:33)

Figure 10:
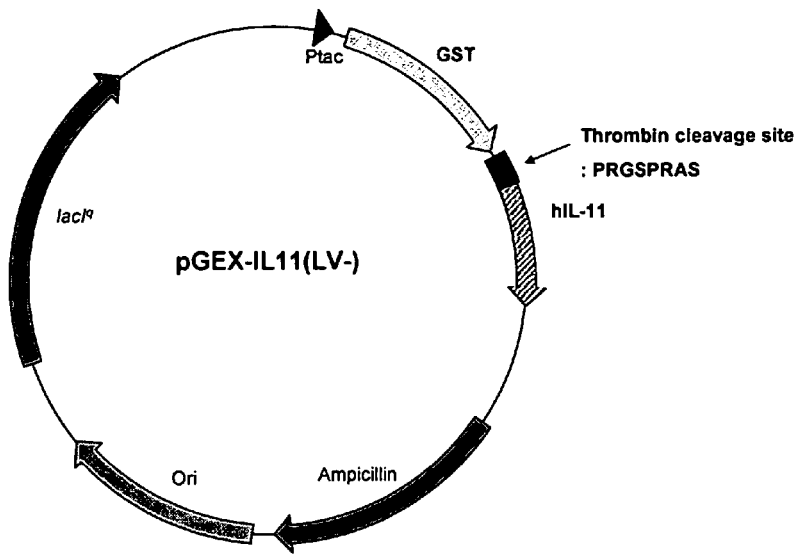
FIG. 10 shows the schematic representation of pGEX-IL11 (LV-) encoding a fusion protein comprising a peptide linker of the invention (SEQ ID NO:7).

The resulting plasmid was named as pGEX-IL11(LV-) (FIG. 10), and used for the production of GST-IL11(LV-).

The amino acid sequence of IL-11(LV-) including the thrombin cleavage site is given below.

Pro-Arg-Gly-Ser-Pro-Arg↓-Ala-Ser-Pro-Asp-Pro-Arg-Ala-Glu-Leu-Asp-Ser-Thr-Val -Leu-Leu-Thr-Arg-Ser-Leu-Leu-Ala-Asp-Thr-Arg-Gln-Leu-Ala-Ala-Gln-Leu-Arg-Asp -Lys-Phe-Pro-Ala-Asp-Gly-Asp-His-Asn-Leu-Asp-Ser-Leu-Pro-Thr-Leu-Ala-Met-Ser -Ala-Gly-Ala-Leu-Gly-Ala-Leu-Gln-Leu-Pro-Gly-Val-Leu-Thr-Arg-Leu-Arg-Ala-Asp -Leu-Leu-Ser-Tyr-Leu-Arg-His-Val-Gln-Trp-Leu-Arg-Arg-Ala-Gly-Gly-Ser-Ser-Leu -Lys-Thr-Leu-Glu-Pro-Glu-Leu-Gly-Thr-Leu-Gln-Ala-Arg-Leu-Asp-Arg-Leu-Leu-Arg -Arg-Leu-Gln-Leu-Leu-Met-Ser-Arg-Leu-Ala-Leu-Pro-Gln-Pro-Pro-Pro-Asn-Pro-Pro -Ala-Pro-Pro-Leu-Ala-Pro-Pro-Ser-Ser-Ala-Trp-Gly-

Gly-Ile-Arg-Ala-Ala-His-Ala -Ile-Leu-Gly-Gly-Leu-His-Leu-Thr-Leu-Asp-Trp-Ala-Val-Arg-Gly-Leu-Leu-Leu-Leu -Lys-Thr-Arg-Leu (SEQ ID NO:34)

The expression plasmid was transformed into *E. coli* BL21. Transformants were inoculated in LB Broth supplemented with ampicillin (50 μg/ml final concentration), and incubated at 37° C. until OD 600 reached 0.5, and IPTG was added to a final concentration of 0.4 mM. Incubation was continued for 3 h, and the cells were harvested by centrifugation. The expression of GST-IL11(LV-) was confirmed by SDS-PAGE. The bacterial pellets were resuspended in 50 mM Tris-HCl buffer, pH 8.0 and lysed by sonication. GST-IL11(LV-) was purified by Glutathione Sepharose 4 Fast Flow from the soluble fraction.

Figure 11:
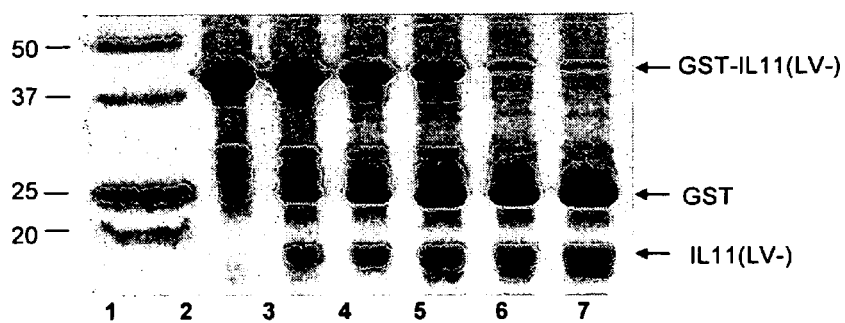
FIG. 11 shows the thrombin cleavage of GST-IL11(LV-).

The purified fusion proteins were digested with thrombin and analyzed by SDS-PAGE. One hundred micrograms of protein samples were subjected to cleavage by 0.5 units thrombin in 25 mM Tris-HCl buffer containing 150 mM NaCl, pH 8, at 20° C. Aliquots were removed from each reaction at various time points (10 min, 30 min, 1 h, 2 h, and 3 h after reaction), and heat-inactivated by boiling for 5 min to stop the reaction. The fusion protein GST-IL11(LV-) (44 kDa) gradually disappeared, and the amount of IL-11(LV-) (18 kDa) increased as reaction time passed (FIG. 11).

To check where the cleavage occurred by thrombin treatment, the protein band containing IL-11(LV-) protein was obtained, and subjected to amino acid sequencing. First, the purified GST-IL11(LV-) protein was treated with thrombin for 3 h, and separated by SDS-PAGE. Then, the proteins in the polyacrylamide gel were transferred to PVDF membrane. After the band containing IL-11(LV-) protein was identified, it was sliced away from the PVDF membrane, and subjected to amino acid sequencing. It was confirmed that the IL-11 (LV-) has the sequence Ala-Ser-Pro-Asp-Pro-Arg-Ala-Glu-Leu-Asp (SEQ ID NO:35) at its N-terminus, suggesting that the Pro-Arg-Gly-Ser-Pro-Arg-Ala-Ser (SEQ ID NO:7) sequence is enough for efficient thrombin cleavage.

EXAMPLE 6

MBP-IL11

Figure 12:
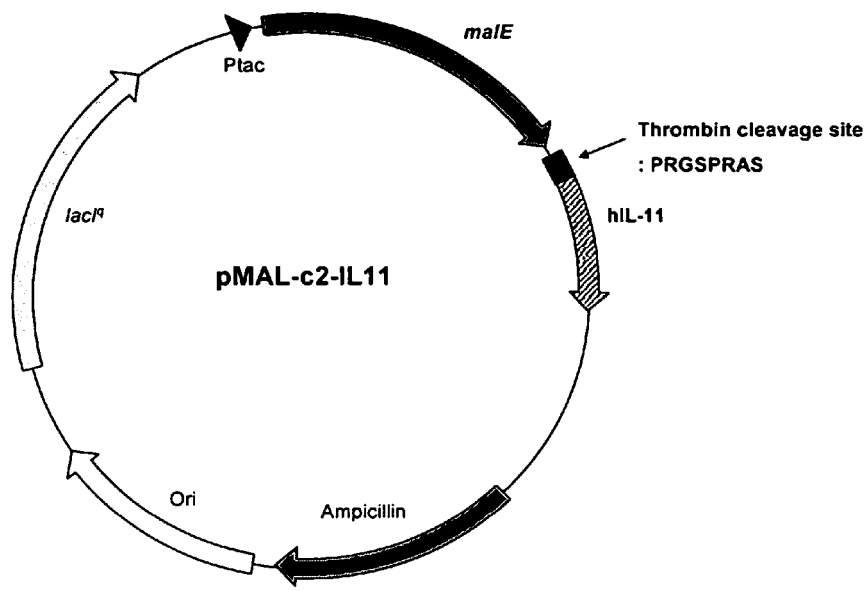
FIG. 12 shows the schematic representation of pMAL-c2-IL11 encoding a fusion protein comprising a peptide linker of the invention (SEQ ID NO:7).

The MBP-IL11 expression plasmid, pMAL-c2-IL11, was constructed by inserting a cDNA of human IL-11 into pMAL-c2 (FIG. 12). A cDNA encoding human IL-11 was obtained from pGEX4T-IL11(A) by PCR. The oligonucleotide sequences for PCR were as follows:

5': GAA TTC CCT CGA GGT TCA CCT CGA GCT TCC (SEQ ID NO:36) EcoRI

3': GTC GAC TCA CAG CCG AGT CTT CAG CAG (SEQ ID NO:37) SalI

The 5' primer was designed to contain the coding sequence for Pro-Arg-Gly-Ser-Pro-Arg↓Ala-Ser (SEQ ID NO:7). The EcoRI/SalI fragment containing IL-11 sequence was cloned into the EcoRI/SalI site of the pMAL-c2 vector, producing pMAL-c2-IL11. Therefore, pMAL-c2-IL111 has the same thrombin cleavage site as pGEX-IL11(LV-) between the maltose binding domain and human IL-11 sequences.

The amino acid sequence of IL-11 downstream of the maltose binding domain including the thrombin cleavage site is given below.

Pro-Arg-Gly-Ser-Pro-Arg↓-Ala-Ser-Pro-Asp-Pro-Arg-Ala-Glu-Leu-Asp -Ser-Thr-Val-Leu-Leu-Thr-Arg-Ser-Leu-Leu-Ala-Asp-Thr-Arg-Gln-Leu-Ala -Ala-Gln-Leu-Arg-Asp-Lys-Phe-Pro-Ala-Asp-Gly-Asp-His-Asn-Leu-Asp-Ser -Leu-Pro-Thr-Leu-Ala-Met-Ser-Ala-Gly-Ala-Leu-Gly-Ala-Leu-Gln-Leu-Pro -Gly-Val-Leu-Thr-Arg-Leu-Arg-Ala-Asp-Leu-Leu-Ser-Tyr-Leu-Arg-His-Val -Gln-Trp-Leu-Arg-Arg-Ala-Gly-Gly-Ser-Ser-Leu-Lys-Thr-Leu-Glu-Pro-Glu -Leu-Gly-Thr-Leu-Gln-Ala-Arg-Leu-Asp-Arg-Leu-Leu-Arg-Arg-Leu-Gln-Leu -Leu-Met-Ser-Arg-Leu-Ala-Leu-Pro-Gln-Pro-Pro-Pro-Asn-Pro-Pro-Ala-Pro -Pro-Leu-Ala-Pro-Pro-Ser-Ser-Ala-Try-Gly-Gly-Ile-Arg-Ala-Ala-His-Ala-Ile -Leu-Gly-Gly-Leu-His-Leu-Thr-Leu-Asp-Trp-Ala-Val-Arg-Gly-Leu-Leu-Leu -Leu-Lys-Thr-Arg-Leu (SEQ ID No:34)

The expression plasmid was transformed into *E. coli* BL21. Transformants were inoculated in LB Broth supplemented with ampicillin (50 μg/ml final concentration), and incubated at 37° C. until OD 600 reached 0.5, and IPTG was added to a final concentration of 0.4 mM. Incubation was continued for 3 h, and the cells were harvested by centrifugation. The expression of MBP-IL11 was confirmed by SDS-PAGE. The bacterial pellets were resuspended in 20 mM Tris-HCl buffer, pH 7.4 containing 200 mM NaCl, 1 mM EDTA, and 1 mM sodium azide and lysed by sonication. The supernatant containing target protein was applied to an amylose (New England Biolabs) affinity column pre-equilibrated with 20 mM Tris-HCl buffer, pH 7.4 containing 200 mM NaCl, and 1 mM EDTA. Following several washes, the bound fusion protein was eluted with 20 mM Tris-HCl buffer, pH 7.4 containing 200 mM NaCl, 1 mM EDTA, and 10 mM maltose.

Figure 13:
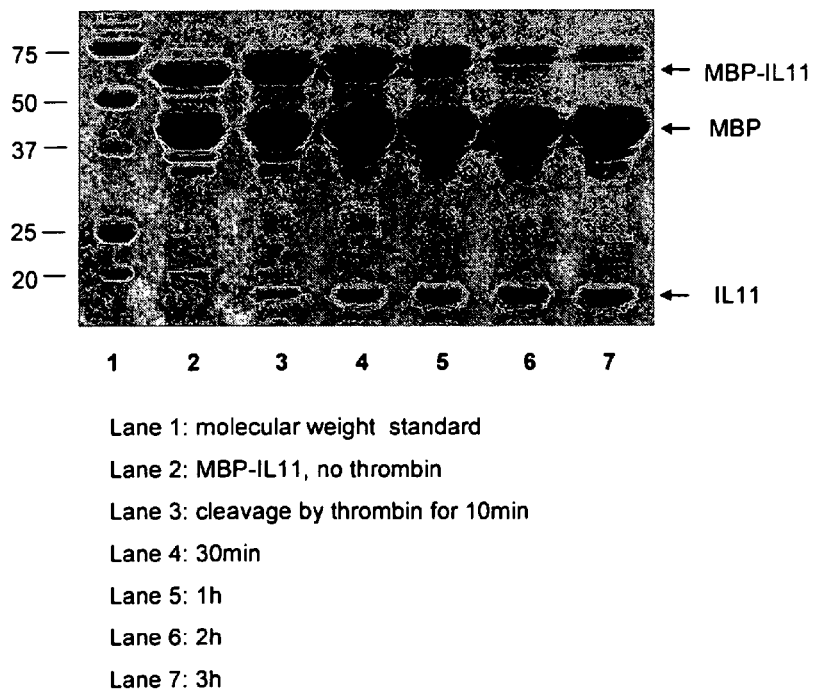
FIG. 13 shows the thrombin cleavage of MBP-IL11.

The purified fusion proteins were digested with thrombin and analyzed by SDS-PAGE. One hundred micrograms of protein samples were subjected to cleavage by 0.5 units thrombin in 20 mM Tris-HCl buffer, pH 7.4 containing 200 mM NaCl, 1 mM EDTA, and 10 mM maltose, at 20° C. Aliquots were removed from each reaction at various time points (10 min, 30 min, 1 h, 2 h, and 3 h after reaction), and heat-inactivated by boiling for 5 min to stop the reaction. The fusion protein MBP-IL11 (60 kDa) gradually disappeared, and the amount of IL11 (18 kDa) increased as reaction time passed (FIG. 13).

To check where the cleavage occurred by thrombin treatment, the protein band containing IL-11 protein was obtained, and subjected to amino acid sequencing. First, the purified MBP-IL11 protein was treated with thrombin for 3 h, and separated by SDS-PAGE. Then, the proteins in the polyacrylamide gel were transferred to PVDF membrane. After the band containing IL-11 protein was identified, it was sliced away from the PVDF membrane, and subjected to amino acid sequencing. It was confirmed that the IL-11 has the sequence Ala-Ser-Pro-Asp-Pro-Arg-Ala-Glu-Leu-Asp (SEQ ID NO:38) at its N-terminus, suggesting that the Pro-Arg-Gly-Ser-Pro-Arg-Ala-Ser (SEQ ID NO:7) sequence is enough for efficient thrombin cleavage.

EXAMPLE 7

HIS-IL11

Figure 14:
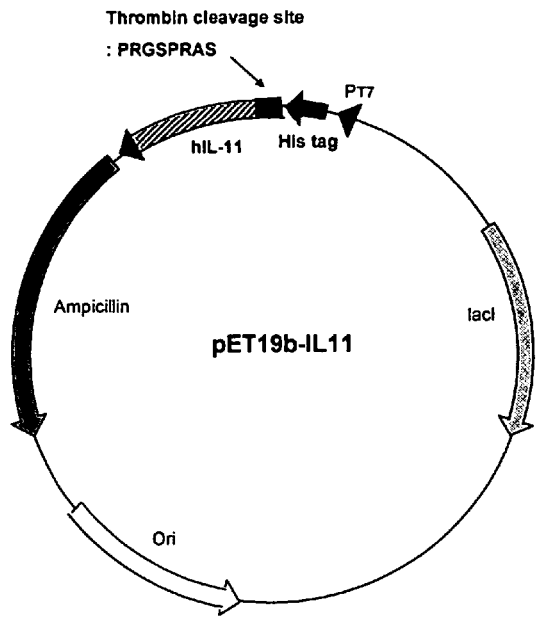
FIG. 14 shows the schematic representation of pET19b-IL11 encoding a fusion protein comprising a peptide linker of the invention (SEQ ID NO:7).

The His-IL11 expression plasmid, pET19b-IL 11, was constructed by inserting a cDNA of human IL-11 into pET-19b (FIG. 14). A cDNA encoding human IL-11 was obtained from pGEX4T-IL11(A) by PCR. The oligonucleotide sequences for PCR were as follows:

5': CAT ATG CCT CGA GGT TCA CCT CGA GCT TCC (SEQ ID NO:39) NdeI

3': GGA TCC TCA CAG CCG AGT CTT CAG CAG (SEQ ID NO:40) BamHI

The 5' primer was designed to contain the coding sequence for Pro-Arg-Gly-Ser-Pro-Arg↓Ala-Ser (SEQ ID NO:7). The NdeI/BamHI fragment containing IL-11 sequence was cloned into the NdeI/BamHI site of the pET19b vector, generating pET19b-IL11. Therefore, pET19b-IL11 has the same thrombin cleavage site as pGEX-IL11(LV-) between the His tag and human IL-11 sequences.

The amino acid sequence of IL-11 downstream of the His tag including the thrombin cleavage site is given below.

Pro-Arg-Gly-Ser-Pro-Arg↓-Ala-Ser-Pro-Asp-Pro-Arg-Ala-Glu-Leu-Asp -Ser-Thr-Val-Leu-Leu-Thr-Arg-Ser-Leu-Leu-Ala-Asp-Thr-Arg-Gln-Leu-Ala -Ala-Gln-Leu-Arg-Asp-Lys-Phe-Pro-Ala-Asp-Gly-Asp-His-Asn-Leu-Asp-Ser -Leu-Pro-Thr-Leu-Ala-Met-Ser-Ala-Gly-Ala-Leu-Gly-Ala-Leu-Gln-Leu-Pro -Gly-Val-Leu-Thr-Arg-Leu-Arg-Ala-Asp-Leu-Leu-Ser-Tyr-Leu-Arg-His-Val -Gln-Trp-Leu-Arg-Arg-Ala-Gly-Gly-Ser-Ser-Leu-Lys-Thr-Leu-Glu-Pro-Glu -Leu-Gly-Thr-Leu-Gln-Ala-Arg-Leu-Asp-Arg-Leu-Leu-Arg-Arg-Leu-Gln-Leu -Leu-Met-Ser-Arg-Leu-Ala-Leu-Pro-Gln-Pro-Pro-Pro-Asn-Pro-Pro-Ala-Pro -Pro-Leu-Ala-Pro-Pro-Ser-Ser-Ala-Try-Gly-Gly-Ile-Arg-Ala-Ala-His-Ala-Ile -Leu-Gly-Gly-Leu-His-Leu-Thr-Leu-Asp-Trp-Ala-Val-Arg-Gly-Leu-Leu-Leu -Leu-Lsy-Thr-Arg-Leu(Seq ID No:34)

The expression plasmid was transformed into *E. coli* BL21 (DE3). Transformants were inoculated in LB Broth supplemented with ampicillin (50 µg/ml final concentration), and incubated at 37° C. until OD 600 reached 0.5, and IPTG was added to a final concentration of 1 mM. Incubation was continued for 3 h, and the cells were harvested by centrifugation. The expression of His-11 was confirmed by SDS-PAGE. The bacterial pellets were resuspended in 20 mM sodium phosphate buffer, pH 7.4 containing 0.5 M NaCl and lysed by sonication. The supernatant containing target protein was applied to a Ni-Sepharose High Performance (Amersham Biosciences) affinity column pre-equilibrated with 20 mM sodium phosphate buffer, pH 7.4 containing 0.5 M NaCl and 20 mM imidazole. Following several washes, the bound fusion protein was eluted with 20 mM sodium phosphate buffer, pH 7.4 containing 0.5 M NaCl and 500 mM imidazole.

Figure 15:
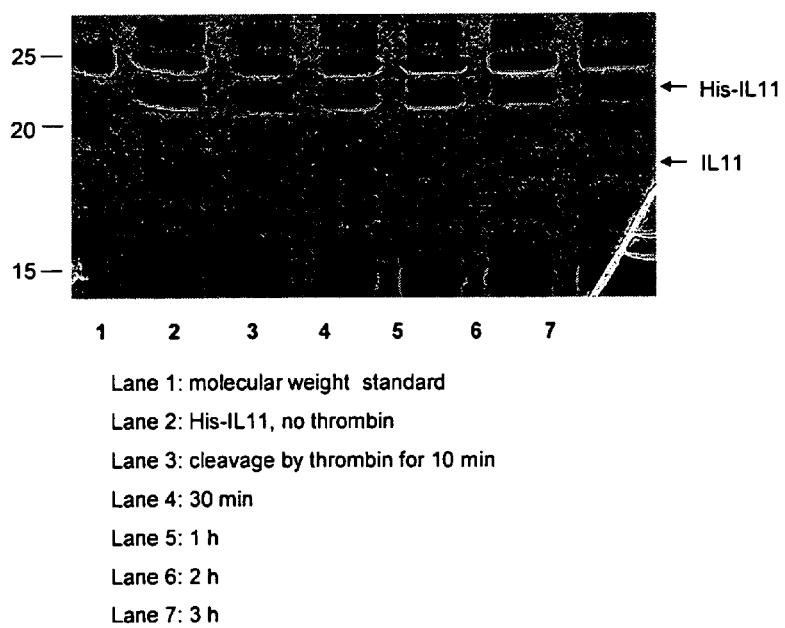
FIG. 15 shows the thrombin cleavage of His-IL11.

The purified fusion proteins were digested with thrombin and analyzed by SDS-PAGE. One hundred micrograms of protein samples were subjected to cleavage by 0.5 units thrombin in 20 mM sodium phosphate buffer, pH 7.4 containing 0.5 M NaCl and 500 mM imidazole, at 20° C. Aliquots were removed from each reaction at various time points (10 min, 30 min, 1 h, 2 h, and 3 h after reaction), and heat-inactivated by boiling for 5 min to stop the reaction. The fusion protein His-IL11 (22 kDa) gradually disappeared, and the amount of IL11 (18 kDa) increased as reaction time passed (FIG. 15).

To check where the cleavage occurred by thrombin treatment, the protein band containing IL-11 protein was obtained, and subjected to amino acid sequencing. First, the purified His-IL11 protein was treated with thrombin for 3 h, and separated by SDS-PAGE. Then, the proteins in the polyacrylamide gel were transferred to PVDF membrane. After the band containing IL-11 protein was identified, it was sliced away from the PVDF membrane, and subjected to amino acid sequencing. It was confirmed that the IL-11 has the sequence Ala-Ser-Pro-Asp-Pro-Arg-Ala-Glu-Leu-Asp (SEQ ID NO:41) at its N-terminus, suggesting that the Pro-Arg-Gly-Ser-Pro-Arg-Ala-Ser (SEQ ID NO:7) sequence is enough for efficient thrombin cleavage.

Having now fully described the invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

---

What is claimed is:

1. A chimeric protein comprising a protein of interest, a fusion partner, and a peptide linker interposed there between, wherein said protein of interest is linked to the N-terminus of said peptide linker and said fusion partner is linked to the C-terminus of said peptide linker or said protein of interest is linked to the C-terminus of said peptide linker and said fusion partner is linked to the N-terminus of said peptide linker,
   wherein the peptide linker consists of the sequence Pro-Arg-Gly-Ser-Pro-Arg-Ala-Ser (SEQ ID NO:7) or the sequence Leu-Val-Pro-Arg-Gly-Ser-Pro-Arg-Ala-Ser (SEQ ID NO:8), and
   wherein said fusion partner is an affinity peptide.

2. The chimeric protein of claim 1, wherein the peptide linker consists of the sequence Pro-Arg-Gly-Ser-Pro-Arg-Ala-Ser (SEQ ID NO:7).

3. The chimeric protein of claim 1, wherein the peptide linker consists of the sequence Leu-Val-Pro-Arg-Gly-Ser-Pro-Arg-Ala-Ser (SEQ ID NO:8).

4. A chimeric protein comprising a protein of interest, a fusion partner, and a peptide linker interposed there between, wherein said protein of interest is linked to the N-terminus of said peptide linker and said fusion partner is linked to the C-terminus of said peptide linker or said protein of interest is linked to the C-terminus of said peptide linker and said fusion partner is linked to the N-terminus of said peptide linker;
   wherein the peptide linker consists of the sequence Pro-Arg-Gly-Ser-Pro-Arg-Ala-Ser(SEQ ID NO:7) or the sequence Leu-Val-Pro-Arg-Gly-Ser-Pro-Arg-Ala-Ser (SEQ ID NO:8)
   wherein said protein of interest is selected from the group consisting of human interleukin (IL)-11, thymosin β4, thymosin α1, IL-2, IL-3, IL-4, IL-5, IL-6, IL-7, IL-8, IL10, IL-13, IL-15, IL-18, Protease-activated receptor 1 (PAR1), PAR3, PAR4, RANTES, stromal cell-derived factor-1α, monocyte chemotactic protein, stem cell factor, FLT-3L, parathyroid hormone, thrombopoictin, epidermal growth factor, basic fibroblast growth factor, insulin-like growth factor, granulocyte-macrophage colony stimulating factor, granulocyte colony stimulating factor, macrophage colony stimulating factor, platelet-derived growth factor, transforming growth factor (TGF)-β1, tumor necrosis factor (TNF)-α, interferon (IFN)-α, IFN-fβ, IFN-γ, hepatocyte growth factor, vascular endothelial growth factor and immunoglobulin heavy chain, wherein said chimeric protein is non-naturally occurring.

5. The chimeric protein of claim 4, wherein said protein of interest is selected from the group consisting of human IL11, thymosin β4, IL-6 and PAR4.

6. The chimeric protein of claim 4, wherein said protein of interest is human IL11.

7. The chimeric protein of claim 4, wherein said fusion partner is an affinity peptide.

8. The chimeric protein of claim 7, wherein said affinity peptide is selected from the group consisting of glutathione-S-transferase (GST), maltose binding protein (MBP), hexa-histidine, T7 peptide, ubiquitin, Flag peptide, c-myc peptide, polyarginine, polycysteine, polyphenylalanine, BTag, galactose binding domain, cellulose binding domain (CBD), thioredoxin, staphylococcal protein A, streptococcal protein G, calmodulin, beta-galactosidase, chloramphenicol acetyltransferase, S-peptide, streptavidin, His-tag, and Strep-tag.

9. The chimeric protein of claim 8, wherein said affinity peptide is selected from the group consisting of GST, MBP and His-tag.

10. The chimeric protein of claim 5, wherein said protein of interest is thymosin β4.

11. The chimeric protein of claim 5, wherein said protein of interest is IL-6.

12. The chimeric protein of claim 5, wherein said protein of interest is PAR4.

13. The chimeric protein of claim 4, wherein the peptide linker consists of the sequence Pro-Arg-Gly-Ser-Pro-Arg-Ala-Ser (SEQ ID NO:7).

14. The chimeric protein of claim 4, wherein the peptide linker consists of the sequence Leu-Val-Pro-Arg-Gly-Ser-Pro-Arg-Ala-Ser (SEQ ID NO:8).

15. The chimeric protein of claim 4, wherein said protein of interest is linked to the N-terminus of said peptide linker and said fusion partner is linked to the C-terminus of said peptide linker.

16. The chimeric protein of claim 4, wherein said protein of interest is linked to the C-terminus of said peptide linker and said fusion partner is linked to the N-terminus of said peptide linker.

17. The chimeric protein of claim 9, wherein said affinity peptide is GST.

18. A chimeric protein comprising a protein of interest, a fusion partner, and a peptide linker interposed there between, wherein said protein of interest is linked to the N-terminus of said peptide linker and said fusion partner is linked to the C-terminus of said peptide linker or said protein of interest is linked to the C-terminus of said peptide linker and said fusion partner is linked to the N-terminus of said peptide linker; said peptide linker consisting of the sequence: Leu-Val-Pro-Arg-Gly-Ser-Pro-Arg-Ala-Ser (SEQ ID NO: 8).

19. The chimeric protein of claim 18, wherein said protein of interest is linked to the N-terminus of said peptide linker and said fusion partner is linked to the C-terminus of said peptide linker.

20. The chimeric protein of claim 18, wherein said protein of interest is linked to the C-terminus of said peptide linker and said fusion partner is linked to the N-terminus of said peptide linker.

21. The chimeric protein of claim 18, wherein said fusion partner is an affinity peptide selected from the group consisting of glutathione-S-transferase (GST), maltose binding protein (MBP), hexahistidine, T7 peptide, ubiquitin, Flag peptide, c-myc peptide, polyarginine, polycysteine, polyphenylalanine, BTag, galactose binding domain, cellulose binding domain (CBD), thioredoxin, staphylococcal protein A, streptococcal protein G, calmodulin, beta-galactosidase, chloramphenicol acetyltransferase, S-peptide, streptavidin, His-tag, and Strep-tag.

22. The chimeric protein of claim 21, wherein said affinity peptide is selected from the group consisting of GST, MBP, and His-tag.

23. The chimeric protein of claim 22, wherein said affinity peptide is GST.

24. The chimeric protein of claim 18, wherein said protein of interest is selected from the group consisting of human IL11, thymosin β4, IL-6 and PAR4.

25. The chimeric protein of claim 1, wherein said affinity peptide is selected from the group consisting of glutathione-S-transferase (GST), maltose binding protein (MBP), hexahistidine, T7 peptide, ubiquitin, Flag peptide, c-myc peptide, polyarginine, polycysteine, polyphenylalanine, BTag, galactose binding domain, cellulose binding domain (CBD), thioredoxin, staphylococcal protein A, streptococcal protein G, calmodulin, beta-galactosidase, chloramphenicol acetyltransferase, S-peptide, streptavidin, His-tag, and Strep-tag.

26. The chimeric protein of claim 25, wherein said affinity peptide is selected from the group consisting of GST, MBP, and His-tag.

27. The chimeric protein of claim 26, wherein said affinity peptide is GST.

28. The chimeric protein of claim 1, wherein said protein of interest is selected from the group consisting of interleukin (IL)-11, thymosin β4, thymosin α1, IL-2, IL-3, IL-4, IL-5, IL-6, IL-7, IL-8, IL-10, IL-13, IL-15, IL-18, Protease-activated receptor 1 (PAR1), PAR3, PAR4, RANTES, stromal cell-derived factor-1α, monocyte chemotactic protein, stem cell factor, FLT-3L, parathyroid hormone, thrombopoietin, epidermal growth factor, basic fibroblast growth factor, insulin-like growth factor, granulocyte-macrophage colony stimulating factor, granulocyte colony stimulating factor, macrophage colony stimulating factor, platelet-derived growth factor, transforming growth factor (TGF)-β1, tumor necrosis factor (TNF)-α, interferon (IFN)-α, IFN-β, IFN-γ, hepatocyte growth factor, vascular endothelial growth factor and immunoglobulin heavy chain.

29. The chimeric protein of claim 28, wherein said protein of interest is selected from the group consisting of human IL11, thymosin β4, IL-6 and PAR4.

30. The chimeric protein of claim 1, wherein said protein of interest is linked to the N-terminus of said peptide linker and said fusion partner is linked to the C-tenninus of said peptide linker.

31. The chimeric protein of claim 1, wherein said protein of interest is linked to the C-terminus of said peptide linker and said fusion partner is linked to the N-terminus of said peptide linker.

* * * * *

UNITED STATES PATENT AND TRADEMARK OFFICE
CERTIFICATE OF CORRECTION

PATENT NO. : 7,585,943 B2
APPLICATION NO. : 11/407336
DATED : September 8, 2009
INVENTOR(S) : Sujeong Kim et al.

It is certified that error appears in the above-identified patent and that said Letters Patent is hereby corrected as shown below:

Column 25, SEQ ID NO: 17, the 146th amino acid: "Tyr" to --Trp--

Column 33, SEQ ID NO: 34, the 144th amino acid: "Tyr" to --Trp--

Signed and Sealed this

Eighth Day of December, 2009

David J. Kappos
*Director of the United States Patent and Trademark Office*